US006553681B2

(12) United States Patent
Ekholm, Jr. et al.

(10) Patent No.: US 6,553,681 B2
(45) Date of Patent: Apr. 29, 2003

(54) METHODS FOR MEASURING A BIO-MATERIAL FOR USE IN AN IMPLANT

(76) Inventors: Carl Roger Ekholm, Jr., 25 Woodsong, Las Flores, CA (US) 92688; Son Nguyen, 8 Varesa, Irvine, CA (US) 92620; Richard L. Peloquin, 3407 Island Lake, Island Lake, IL (US) 60042; Robert Gliniecki, 9604 Fox Trail, Spring Grove, IL (US) 60081; Todd Baeten, 1920 Country Dr., Apt. 301, Grayslake, IL (US) 60030; Suzanne E. Graumlich, 3 Clover, Irvine, CA (US) 92604; Steven Eric Backer, 3606 Park La., Newport Beach, CA (US) 92663

( * ) Notice: Subject to any disclaimer, the term of this patent is extended or adjusted under 35 U.S.C. 154(b) by 6 days.

(21) Appl. No.: 10/135,717

(22) Filed: Apr. 30, 2002

(65) Prior Publication Data

US 2002/0157271 A1 Oct. 31, 2002

Related U.S. Application Data

(63) Continuation of application No. 09/515,113, filed on Feb. 29, 2000.

(51) Int. Cl.[7] .................................................. G01B 5/20
(52) U.S. Cl. ............................. 33/551; 33/511; 702/21; 623/2.13
(58) Field of Search ...................... 33/551, 552, 553, 33/554, 501.02, 511, 121, 123; 623/2.12, 2.13; 702/19, 21, 170

(56) References Cited

U.S. PATENT DOCUMENTS

| 365,873 A | 7/1887 | Spence et al. |
| 1,012,372 A | 12/1911 | Landenberger |
| 1,688,308 A | 10/1928 | Harding |

(List continued on next page.)

FOREIGN PATENT DOCUMENTS

| WO | WO 0133420 | 2/1985 |
| WO | WO 97/21069 | 6/1997 |

OTHER PUBLICATIONS

Sacks, "Biaxial Mechanical Behavior of Fixed Bovine Pericardium," Fifth World Biomaterials Congress, Toronto, Canada, May 29–Jun. 2, 1996.

Simionescu, et al., "Mapping of Glutaraldehyde–Treated Bovine Pericardium and Tissue Selection for Bioprosthetic Heart Valves," Journal of Biomedical Materials Research, vol. 27, 697–703, 1993.

(List continued on next page.)

*Primary Examiner*—G. Bradley Bennett

(57) ABSTRACT

A system and method to facilitate thickness measurement of bio-material workpiece, preferably a sheet, and to topographically map the sheet into similar thickness zones for later use. In particular, the system may include a three-axis programmable controller for manipulating a bio-material workpiece with respect to a thickness measurement head. The measurement head may include a plurality of sensors for simultaneous measurement of a plurality of points, with the sensors being adapted to contact the sheet or not. A robust human-machine interface is also provided for process control, preferably including a touch-screen monitor. A marking head may be provided for marking the zones or otherwise indicating the thickness in different areas. Two platens are desirably used in parallel for increased throughput; the workpiece on one platen may be measured while the other is marked. The system and method are especially suited for assessing and marking pericardial tissue for forming heart valve leaflets. The system may also include logic that analyzes the thickness data and generates a thickness map of the sheet divided into similar thickness zones from which similarly sized leaflets can be cut. A preferred thickness of leaflet may be input with the logic selecting the zones to maximize the available tissue for that size of leaflet.

23 Claims, 13 Drawing Sheets

U.S. PATENT DOCUMENTS

| | | |
|---|---|---|
| 2,122,945 A | 7/1938 | Kleinschmidt |
| 2,856,582 A | 10/1958 | Anderson |
| 3,110,112 A | 11/1963 | Dalgleish |
| 4,060,734 A | 11/1977 | Tilley et al. |
| 4,199,255 A | 4/1980 | Wilson et al. |
| 4,360,887 A | 11/1982 | Wilson et al. |
| 4,388,735 A | 6/1983 | Ionesuc et al. |
| 4,687,483 A | 8/1987 | Fischer et al. |
| 4,725,961 A | 2/1988 | Pearl |
| 4,876,758 A | 10/1989 | Rolloff et al. |
| 4,972,351 A | 11/1990 | Reger et al. |
| 5,037,434 A | 8/1991 | Lane |
| 5,089,971 A | 2/1992 | Gerber |
| 5,376,110 A | 12/1994 | Tu et al. |
| 5,546,323 A * | 8/1996 | Bacus et al. ............ 702/170 |
| 5,549,666 A | 8/1996 | Hata et al. |
| 5,613,982 A | 3/1997 | Goldstein |
| 5,640,779 A | 6/1997 | Rolloff et al. |
| 5,718,012 A | 2/1998 | Cavallaro |
| 6,160,264 A | 12/2000 | Rebiere |
| 6,245,105 B1 * | 6/2001 | Nguyen et al. ............ 623/2.13 |
| 6,378,221 B1 * | 4/2002 | Ekholm et al. ............ 33/551 |
| 6,413,275 B1 * | 7/2002 | Nguyen et al. ............ 623/2.13 |

OTHER PUBLICATIONS

Zioupos, et al., "Anisotropic Elasticity and Strength of Glutaraldehyde Fixed Bovine Pericadium for Use in Pericardial Bioprosthetic Valves," Journal of Biomedical Materials Research, vol. 28, 49–57, 1994.

"The Carpentier–Edwards Perimount Pericardial Bioprosthesis—Time is the Most Important Text, " Baxter, No date.

* cited by examiner

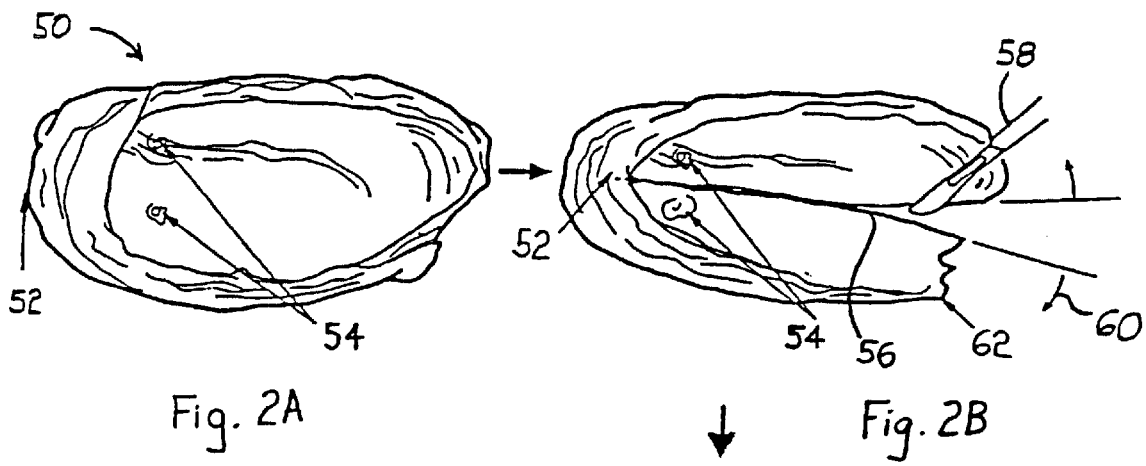
Fig. 2A    Fig. 2B
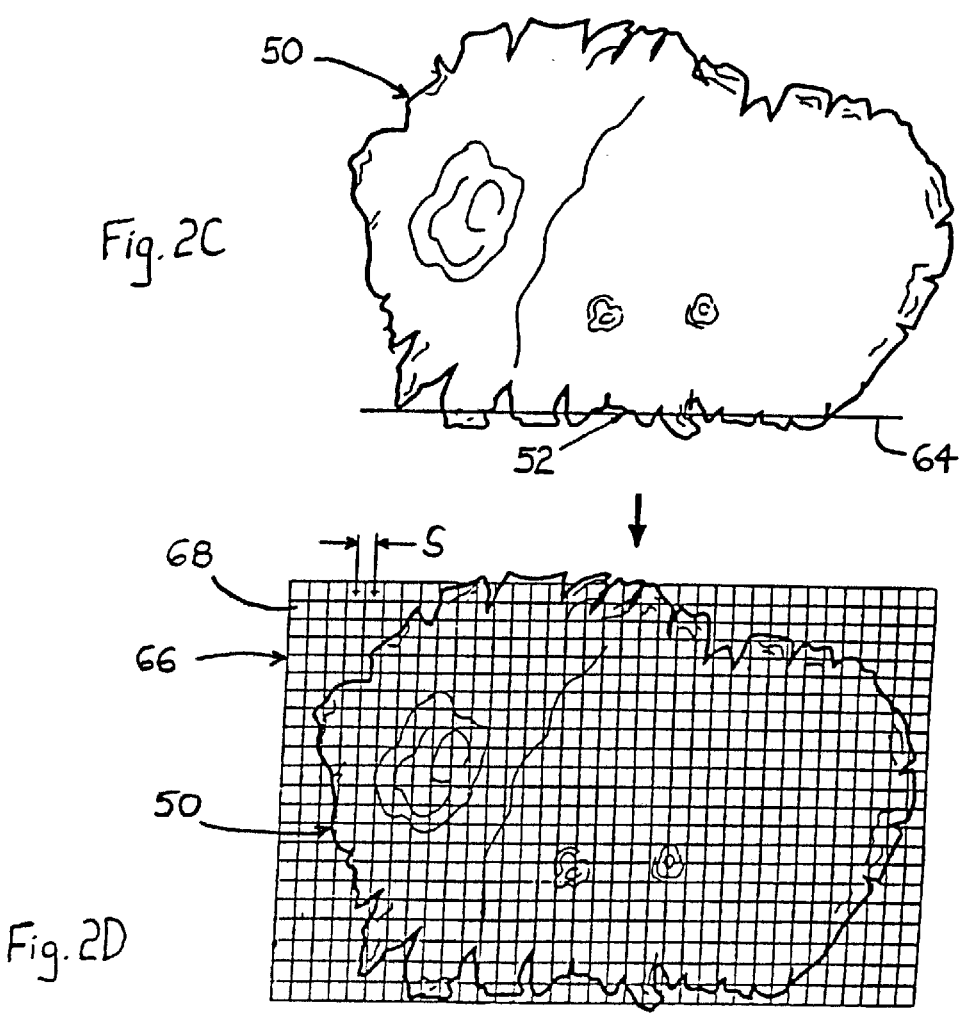
Fig. 2C
Fig. 2D

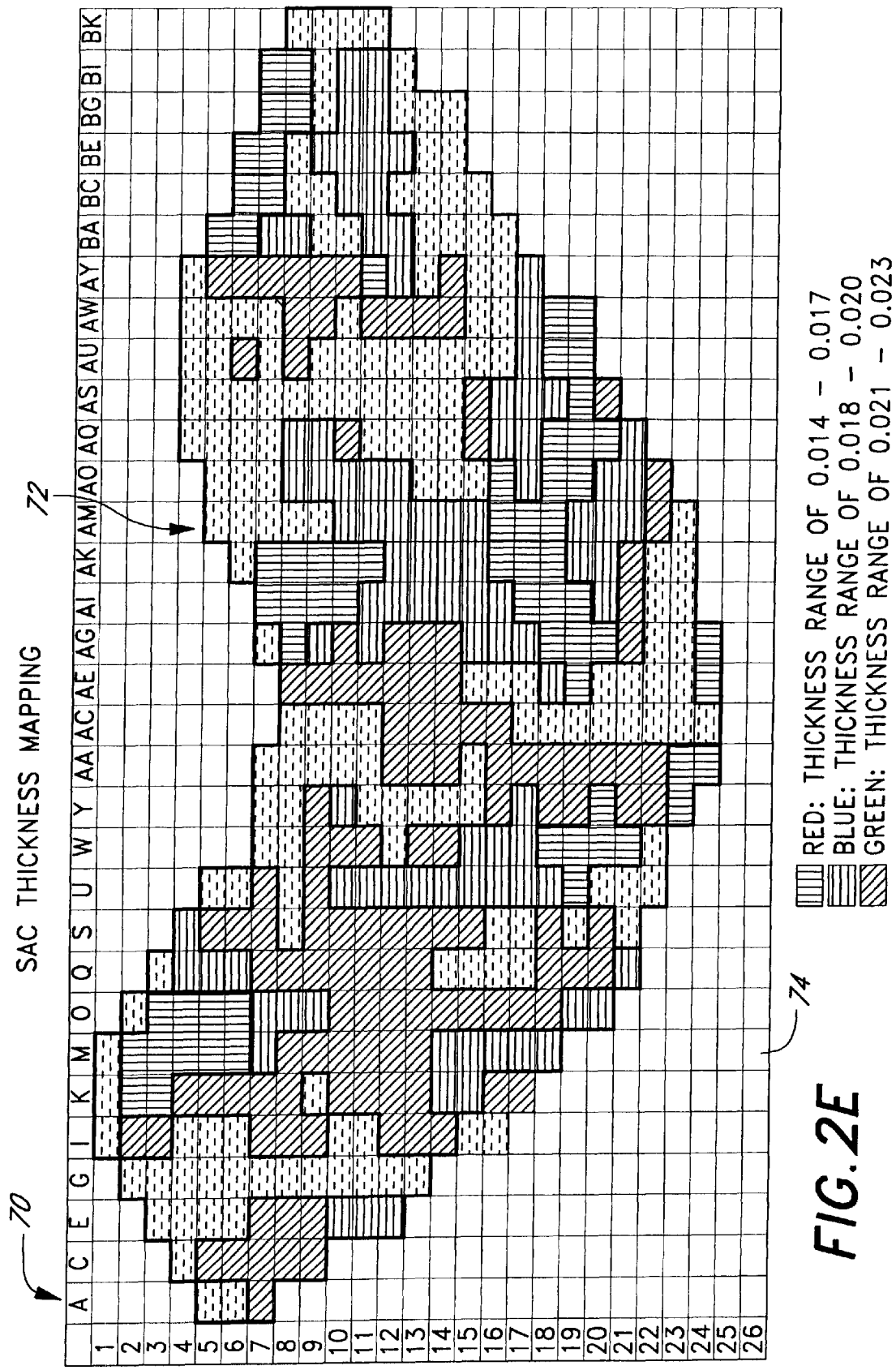

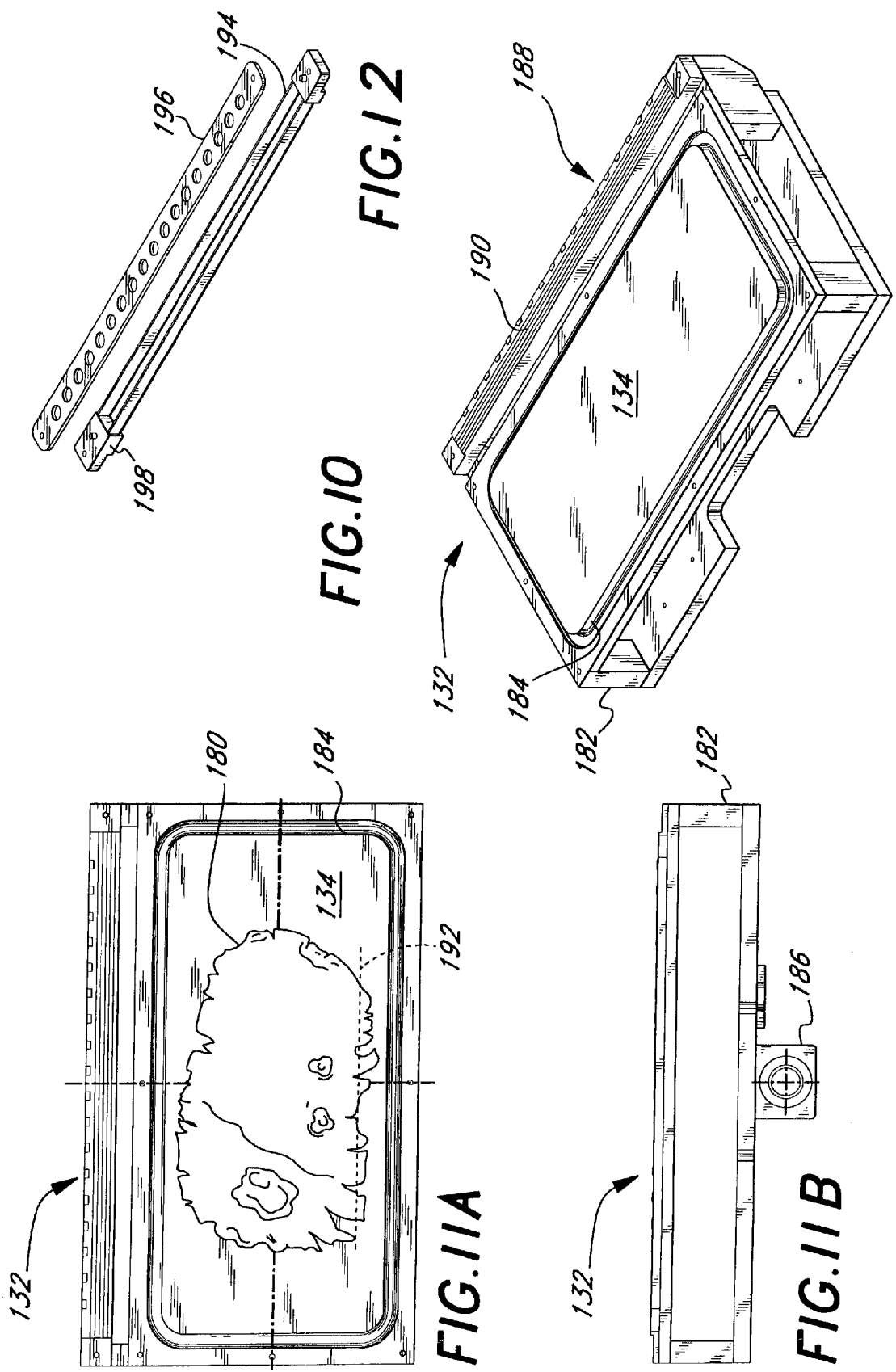

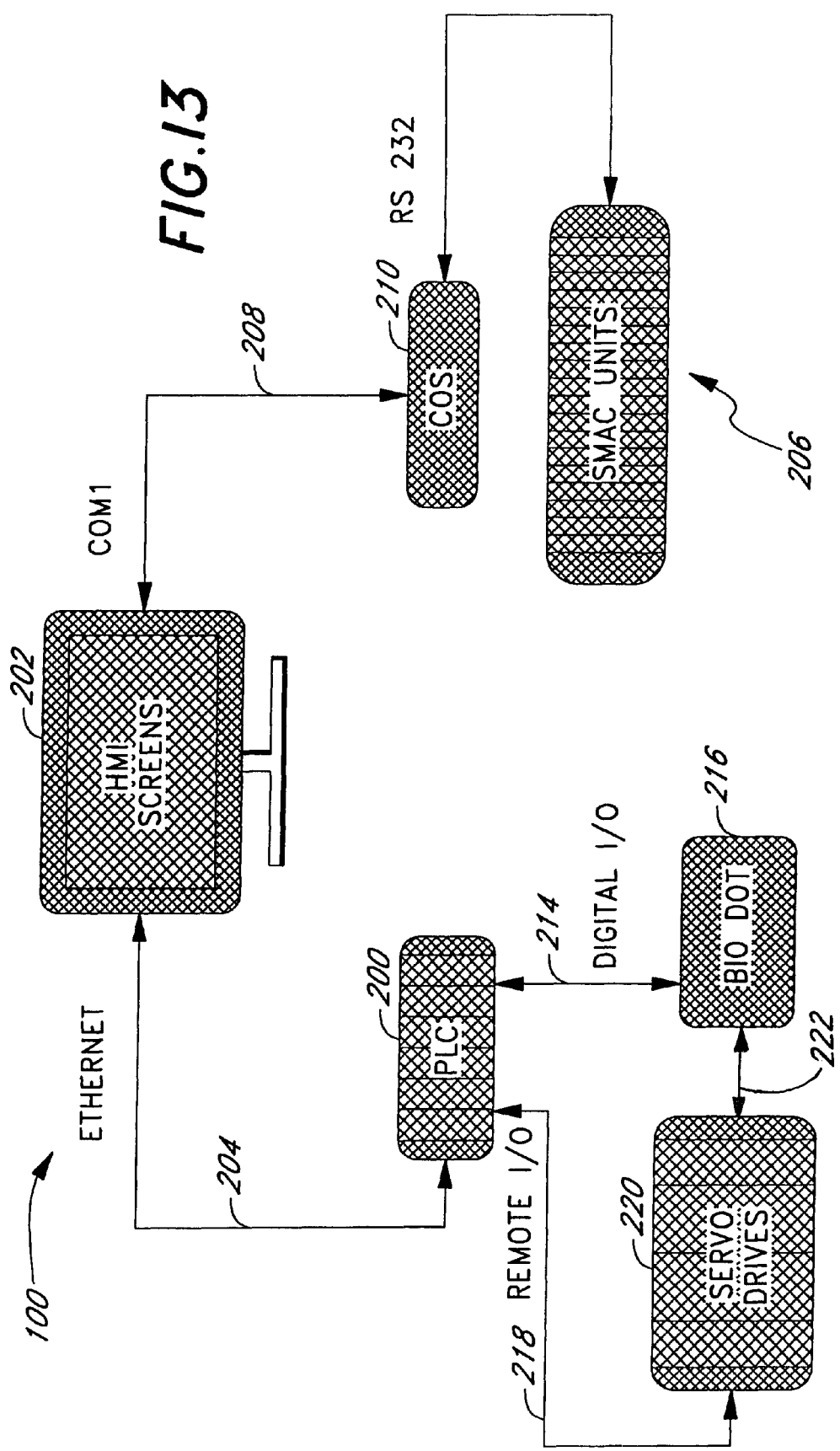

METHODS FOR MEASURING A BIO-MATERIAL FOR USE IN AN IMPLANT

RELATED APPLICATION

The present is a continuation of U.S. application Ser. No. 09/515,113, filed Feb. 29, 2000, entitled "SYSTEMS AND METHODS FOR MAPPING AND MARKING THE THICKNESS OF BIOPROSTHETIC SHEET."

FIELD OF THE INVENTION

The present invention relates to systems and methods for measuring the thickness of sheet-like bio-materials and, in particular, to an improved pericardial tissue mapping and marking system and methods therefore, especially for measuring tissue to be used for making prosthetic heart valve leaflets.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid, and pulmonary valves. Prosthetic heart valves can be used to replace any of these natural valves. The two primary types of prosthetic heart valves known in the art are mechanical valves and bio-prosthetic valves. Bio-prosthetic valves may be formed from an intact, multi-leaflet porcine (pig) heart valve, or by shaping a plurality of individual leaflets out of bovine pericardial tissue or other materials, and combining the leaflets to form the valve. The present invention provides systems and methods for assessing and preparing material for leaflets in bio-prosthetic valves.

The pericardium is a sac around the heart of vertebrate animals, and bovine (cow) pericardium is commonly used to make individual leaflets for prosthetic heart valves. The bovine pericardium is first harvested from the animal and then chemically fixed to crosslink collagen and elastin molecules in the tissue and increase the tissue durability, before being cut into leaflets. Various physical characteristics of the tissue may be examined before or after fixation.

One drawback faced by a patient having an implanted bio-prosthetic heart valve is the potential for calcification of the leaflets if the valve remains in place for an extended period of time (more than ten years). Calcification tends to make the leaflets less flexible. A significant amount of research has been accomplished in mitigating calcification of bovine pericardial leaflets to lengthen the useable life of the heart valve. Calcification may reduce the performance of the heart valve, and thus, the highest quality materials and design in the heart valve is required to forestall a failure of the valve from excessive calcium deposits.

One aspect of designing heart valves which is very important in improving their performance is the selection of the pericardial tissue used in the leaflets. In all heart valves, the natural action of the flexible heart valve leaflets, which seal against each other, or co-apt, is desirable. The difficulty in simulating the leaflet movement of an actual heart valve (especially a mitral valve) in a prosthetic valve is that the leaflets used are "inanimate." There are no muscular attachments to the leaflets as in the natural valve, and the prosthetic leaflets must co-apt to function properly solely in response to the fluid pressures within the heart chambers. Indeed, natural coaptation of the leaflets in bio-prosthetic valves comprising a plurality of individual leaflets sewn together is particularly difficult, even when compared to inanimate but intact valves, such as harvested porcine valves.

Despite the drawbacks of artificial heart valve material, over twenty years of clinical experience surrounding implanted artificial heart valves has produced a proven track record of success. Research in extending the useful life of the bio-prosthetic valves continues, however. Much of this research involves the mechanical properties of fresh or fixed bovine pericardium.

A good discussion of the various physical properties of fixed bovine pericardium is given in Simionescu, et al, Mapping of Glutaraldehyde-Treated Bovine Pericardium and Tissue Selection For Bio-prosthetic Heart Valves, Journal of Bio-Medical Materials Research, Vol. 27, 697–704, John Wiley & Sons, Inc., 1993. Simionescu, et al., recognized the sometimes striking variations in physical properties of the pericardial tissue, even in the same pericardial sac. Their research mapped out areas in individual pericardial sacs and tested those areas for various properties to determine the optimum area on the tissue from which to cut heart valve leaflets. Simionescu, et al. measured the thickness of the pericardial sacs at 5 mm increments and plotted the resulting values on a paper template identical in shape and size to the sac. On other templates, parameters such as the suture holding power, fiber orientation, and shrinkage temperature were mapped. After superimposing all of the templates, optimum areas from which to cut leaflets were identified. Simionescu, et. al., utilized a manual thickness measuring tool similar to that described below with respect to FIG. 1.

A number of steps in a typical commercial process for preparing pericardial tissue for heart valve leaflets is illustrated in FIG. 1. First, a fresh pericardial sac 20 is obtained from a regulation slaughterhouse. The sac 20 is then cut open along predetermined anatomical landmarks, as indicated at 22. The sac is then flattened at 24 and typically cleaned of excess fat and other impurities. After trimming obviously unusable areas, a window 26 of tissue is fixed, typically by immersing in an aldehyde to cross-link the tissue, and then quarantined for a period of about two weeks. Rough edges of the tissue window 26 are removed and the tissue bio-sorted to result in a tissue section 28. The process of bio-sorting involves visually inspecting the window 26 for unusable areas, and trimming the section 28 therefrom. Subsequently, the section 28 is further cleaned as indicated at 30.

The section 28 is then placed flat on a platform 32 for thickness measurement using a contact indicator 34. The thickness is measured by moving the section 28 randomly around the platform 32 while a spindle 36 of the indicator 34 moves up-and-down at various points. The thickness at each point is displayed at 38 and recorded mentally by the operator. After sorting the measured sections 28 by thickness, as indicated at 40, leaflets 42 are die cut from the sections, with thinner leaflets 42 generally being used for smaller valves, and thicker leaflets being used for larger valves. Of course, this process is relatively time-consuming and the quality of the final leaflets is dependent at several steps on the skill of the technician. Moreover, the number of leaflets obtained from each sac is inconsistent, and subject to some inefficiency from the manual selection process.

More recently, Baxter International Inc. has added a sophisticated leaflet selection method into its tissue valve manufacturing process. The method includes applying a load to each leaflet, as opposed to pericardial tissue in bulk, and recording the strain response. The results of the load test in combination with a droop test can be used to group similar leaflets. Such a method is disclosed in U.S. Pat. No. 5,961, 549 to Huynh, issued Oct. 5, 1999, and entitled, "PROSTHETIC HEART VALVE LEAFLET SELECTION METHOD AND APPARATUS". Although this method improves the quality of the resulting combination of leaflets, because of the existing inefficiencies in the process of supplying tissue from which to cut the leaflets, the subsequent filter of leaflet selection further reduces the total usable leaflet output such that costs are increased.

Despite much research into the characteristics of bovine pericardium and leaflets, there remains a need for a system and method for rapidly and reliably characterizing material, especially pericardial tissue, for use in fabricating heart valve leaflets.

SUMMARY OF THE INVENTION

The present invention provides a method of measuring the thickness of a bio-material sheet for use in bioprostheses, such as heart valves, grafts, and the like. The method involves mapping the thickness of the sheet and marking the sheet into areas or zones of similar thickness. The measuring, mapping, and marking steps can all be carried out automatically with a system that receives the sheet and translates it under a measurement head and a marking head, with the mapping function being performed by a connected computer and associated software. In a preferred embodiment, the bio-material sheet is bovine pericardium and from which heart valve leaflets are to be cut. The method further may include providing input as to a preferred thickness needed, and selecting the zones based on that input to maximize the preferred thickness marked.

In one aspect of the invention, a method of measuring the thickness of a bio-material sheet comprises first flattening the sheet on a sanitary surface, simultaneously measuring the thickness of a plurality of points on the flattened sheet, and automatically recording the measured thicknesses of the plurality of points. The step of simultaneously measuring desirably includes measuring at least three points, and more preferably at least ten points, on the flattened sheet. Further, the step of simultaneously measuring may occur more than once, wherein the plurality of points in each step of simultaneously measuring is arrayed along a line, and wherein each line is spaced from the line in a preceding or subsequent step of measuring so as to obtain a two-dimensional array of measured points on the sheet.

In another aspect of the invention, the method may further include providing a measurement head positioned normal to the surface, and relatively displacing the surface and measurement head in a direction parallel to the surface between each successive step of simultaneously measuring. A base may be provided upon which both the surface and measurement head are mounted, and the step of relatively displacing may comprise translating the measurement head relative to the base between each successive step of a simultaneously measuring. Desirably, a programmable controller controls movement of the measurement head.

The step of simultaneously measuring may include simultaneously contacting a plurality of points on a surface of the sheet facing away from the surface, preferably with a plurality of coil-driven shafts and monitoring the position of each shaft. Or, the step of simultaneously contacting includes simultaneously contacting the surface of the sheet with a plurality of free-sliding pins and monitoring the position of each pin.

In another aspect, the present invention provides a method of mapping the topography of a bio-material sheet by first providing a measuring system including a sanitary surface and a measurement head positioned normal to and spaced from the surface, wherein the measurement head includes a plurality of sensors adapted to measure distance along spaced axes normal to the surface. The sheet of bio-material is flattened on the surface, and the thickness of the sheet at a plurality of points is measured using the sensors. The thickness data is then used to create a topographical map of the sheet. The method, further may include marking the sheet to indicate the thickness of the plurality of points corresponding to the topographical map. Also, areas of different thickness may be marked on the sheet. In a preferred embodiment, the sheet is bovine pericardium and the step of marking areas of different thicknesses includes identifying discrete zones of similar thickness that are large enough from which to cut a heart valve leaflet. The method may involve controlling the marking with a computer, supplying the computer with information regarding a preferred thickness of heart valve leaflet, and controlling the marking based on the preferred leaflet thickness information so as to maximize the number of discrete zones of the preferred leaflet thickness that are marked.

In a still further aspect, the invention provides a method of automated mapping of a bio-material sheet to indicate discrete zones from which to cut heart valve leaflets, comprising measuring the thickness of a plurality of points on a flattened sheet, automatically recording the measured thicknesses of the plurality of points, and using the recorded thicknesses to mark discrete zones of the sheet that are large enough from which to cut heart valve leaflets. The method desirably includes determining an acceptable thickness range for each of a number of sizes of heart valve leaflets; and determining an acceptable minimum size of the discrete zones for each of a number of sizes of heart valve leaflets. Where the plurality of points is a two-dimensional array, a plurality of planar units are each centered on one of the measured points, and each discrete zone comprises a plurality of contiguous planar units. Each discrete zone may be selected so that at least some of the planar units within that discrete zone have a measured thickness within the acceptable thickness range for the corresponding heart valve leaflet. Finally, the method further may include marking the discrete zones on the sheet so as to maximize the number of discrete zones of the preferred leaflet thickness that are marked.

A system for measuring the thickness of a bio-material sheet is also provided, comprising a base adapted to be fixed with respect to a support floor, a sanitary platen mounted on the base, and a measurement head mounted on the base and positioned normal to and spaced from the platen. The measurement head includes a plurality of sensors adapted to measure distances along spaced measurement axes disposed normal to the platen, and the sensors are adapted to measure the thickness of a bio-material sheet that has been placed on the platen. The system may further include a movable carriage on which is defined the platen, and a first mechanism configured to relatively displace the platen and measurement head across the platen to enable each sensor to measure the thickness of the sheet at more than one point. Desirably, the platen defines a planar surface on which the bio-material sheet is measured, and the first mechanism enables relative linear translation of the planar surface and measurement head, preferably relative to the base along a first axis parallel to the planar surface. A second mechanism may be provided to relatively displace the planar surface and measurement head along a second axis parallel to the planar surface and perpendicular to the first axis, and desirably the second mechanism translates the planar surface relative to the base along the second axis. A third mechanism may permit relative displacement of each of the sensors on the measurement head along the respective parallel measurement axes disposed normal to the planar surface.

In the system as described above, the sensors each preferably include a tip for contacting a surface of the sheet facing away from the platen. Further, the third mechanism desirably includes a plurality of coil-driven shafts, one per sensor, with the tips positioned at the end of the shafts, and a position detector for monitoring the position of each shaft.

Still another aspect of the invention is a system for topographically mapping the thickness of a bio-material sheet, comprising:

- a measurement head adapted to measure the thickness of a plurality of points on the sheet;
- a computer connected to receive data corresponding to the thickness of the sheet at the plurality of points; and
- software loaded on the computer and configured to analyze the data and identify discrete areas of similar thickness on the sheet.

The system may also include a marking head for marking the discrete areas of similar thickness directly on the bio-material sheet. Where the bio-material sheet is suitable for forming heart valve leaflets therefrom, the system further includes a human-machine interface enabling the computer to be supplied with a value of a preferred thickness of heart valve leaflet. The software is configured to control the marking head to maximize the number of discrete zones of the preferred leaflet thickness that are marked. Preferably, the human-machine interface comprises a touch-screen monitor, and the marking head comprises an ink jet type of dye dispenser.

In a particularly preferred embodiment, therefore, the present invention provides a three-axis computer-controlled positioning system, an array of programmable linear actuators, a high-performance dispenser for tissue marking, a PC-based data acquisition and processing system, a human-machine interface (HMI), and a central programmable logic controller (PLC) to control the overall system. A thickness measurement is made by placing the tissue sample on a flat stainless-steel measurement plate. Mechanical holders may or may not be used to retain the tissue sample on the plate. The thickness of the tissue sample is determined by touching the tissue with the actuator rod in a raster pattern across the surface of the sample. A three-axis motion system is used to translate the linear actuators in one direction (X) while the position of the measurement plate (and thus the sample) is incremented along a second axis (Y). The actuators and the dispensing head translate along the third axis (Z) with respect to the plate for tissue measurement and/or marking. At each point in the measurement, the positions of the actuator rods are digitized and stored. Following data collection, this information is processed to calculate the thickness of the tissue at each point in the measurement process. Based on these measurements, a thickness map is generated and used to identify tissue thickness areas for tissue zone marking and cutting.

A further understanding of the nature and advantages of the invention will become apparent by reference to the remaining portions of the specification and drawings.

BRIEF DESCRIPTION OF THE DRAWINGS

FIGS. 2A–2F illustrate a sequence of steps of the present invention for preparing, measuring and mapping the thickness of bovine pericardial tissue prior to forming leaflets from the tissue;

FIG. 10 is a perspective view of a platen on which sheet-like bio-materials are positioned for measurement in the apparatus of FIG. 5;

FIGS. 11A–11B are plan and elevational views, respectively, of the platen of FIG. 10, with FIG. 11A illustrating a pericardial sac positioned flat thereon;

FIG. 12 is a perspective exploded view of an exemplary measurement tool cleaning apparatus;

FIG. 13 is a schematic view of the various components and interconnections of the apparatus of FIG. 5;

DESCRIPTION OF THE PREFERRED EMBODIMENTS

The present invention provides systems and methods for measuring, mapping and marking the thickness of a bio-material, in particular a sheet bio-material. The term "bio-material" pertains to any material that is suitable for implant in the human body, and is synonymous with bioprosthetic material. For example, suitable bio-materials include, but are not limited to, bovine or other mammalian pericardium, biocompatible material such as polyester, synthetic matrices having collagenous growth thereon, etc.. Although the invention is described and illustrated in terms of an automated system for measuring, mapping and marking a bio-material, various aspects of the invention could be accomplished by manual means. For example, existing manual measurement methods could be used to compile the thickness data needed for the mapping and marking functions of the system. Indeed, the measuring, mapping, and marking techniques described herein could all be accomplished manually. Finally, although the invention is described specifically in terms of assessing a sheet of bovine pericardium for forming heart valve leaflets, the invention is also suitable for forming other bioprosthetic implants or components, including ventricular patches, skin grafts, etc..

Measuring and Mapping Steps

Figure 1:
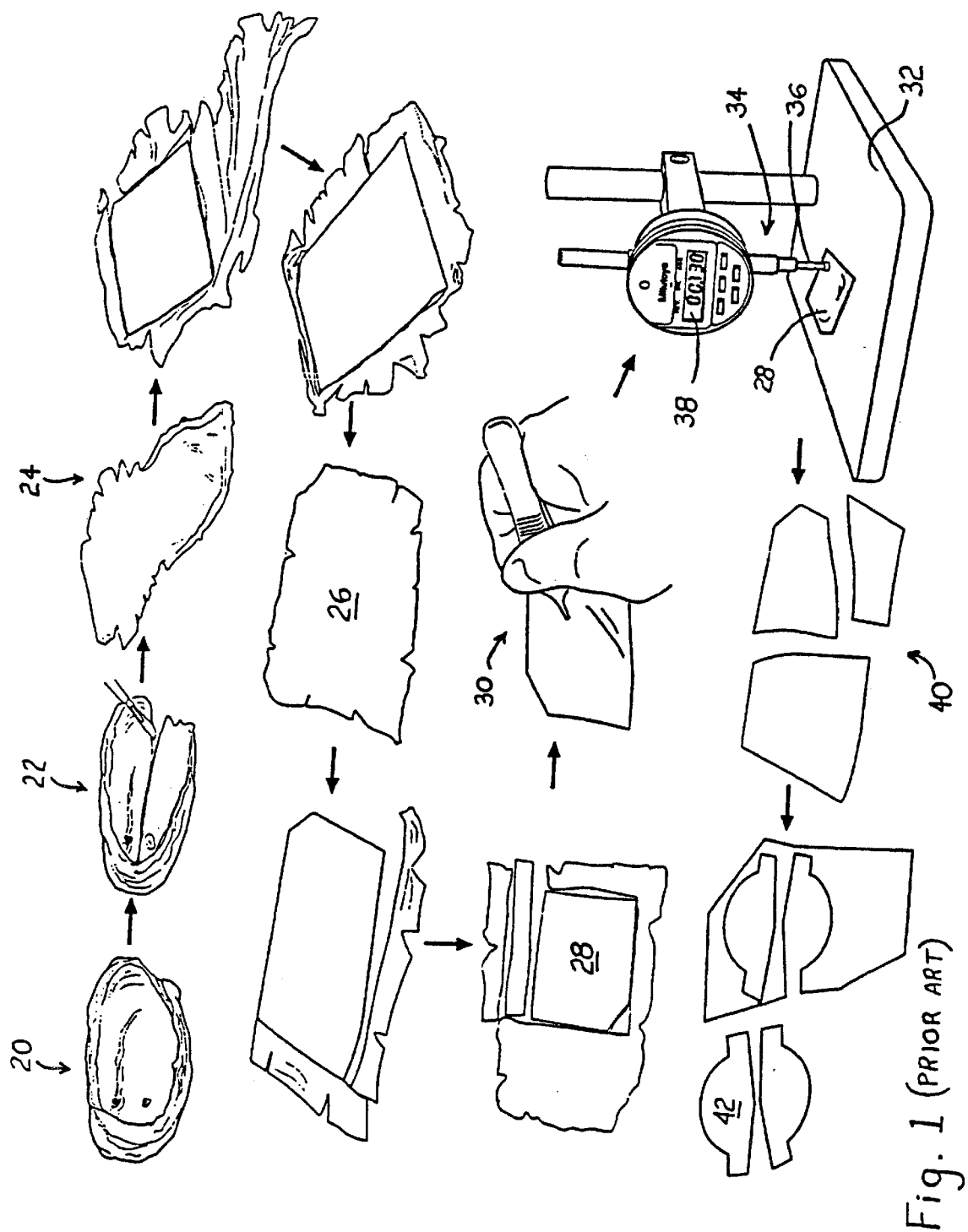
FIG. 1 illustrates a sequence of prior art steps for preparing and measuring the thickness of bovine pericardial tissue prior to forming leaflets from the tissue.
Figure 2F:
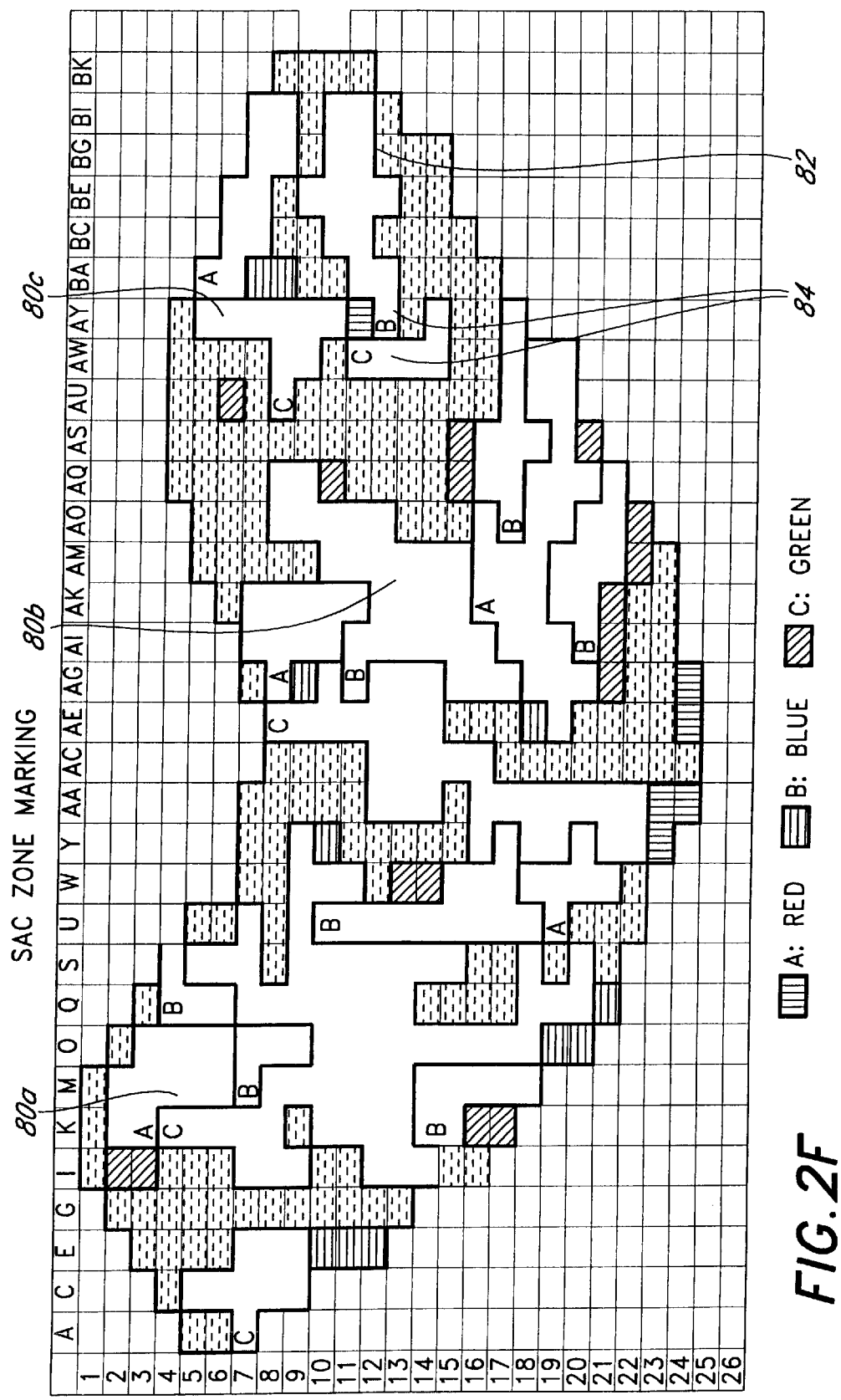

With reference to FIGS. 2A–2F, a sequence of steps in the preparation, thickness measurement, and mapping of a sac 50 of bovine pericardium is shown. First, as seen in FIG. 2A, the sac 50 is harvested at a regulation slaughterhouse. Although each sac 50 is unique, certain anatomical characteristics are shared; including an apex 52 and a pair of sternopericardial ligaments 54. The sac 50 arrives from the slaughterhouse in a three-dimensional sac shape, and must be severed along a cut line 56 using a scalpel 58, as seen in FIG. 2B. The sac is opened up, as indicated by the arrows 60 in FIG. 2B, and flattened into the configuration shown in FIG. 2C. FIG. 2B also illustrates a base 62 which will be used in conjunction with the apex 52 to define a base-apex line 64 seen on the flattened sac 50. The base-apex line 64 provides an approximate indication of the fiber orientation of the sac 50, which will be important during the ultimate step of cutting heart valve leaflets (or other structure) from the sac. The pericardial sac 50 is desirably fixed with a buffered solution of glutaraldehyde or other fixative, quarantined and then cleaned.

FIG. 2D illustrates the flattened sac 50 having a measurement grid pattern 66 superimposed thereon. The measurement grid pattern 66 shown comprises a two-dimensional rectangular array of square units 68, although other grid patterns could be used. As will be explained in detail below, a thickness measurement of the sac 50 is taken at the center point of each of the square units 68 so as to topographically map the entire sac. The center-to-center spacing S is seen in FIG. 2D and can be varied depending on the map resolution desired. In an exemplary embodiment, the spacing S is approximately 9.5 mm (0.375 in). The grid pattern 66 shown encompasses a majority of the sac 50, but does not extend much beyond the outlines of sac. Again, as will be seen below, the grid pattern 66 can be widened further beyond the sac as desired.

After the thickness of the sac 50 is measured at the center point of each of the square units 68, a two-dimensional data grid 70 having a topographical thickness map 72 of the sac 50 is produced, as seen in FIG. 2E. Again, this data grid 70 and map 72 can be produced by hand or automatically using computer logic. Preferably, as will be explained, the data grid 70 and map 72 are automatically generated by software on a computer associated with the physical measurement apparatus. The thickness of the sac 50 in each of the square units 68 is transposed on to the data grid 70 as a color within one of the grid units 74. An exemplary topographical map 72 is shown, with the various thicknesses of the pericardial sac 50 indicated by different color symbols, as explained by the legend. There are four different colors used (other than the white border) corresponding to a different thickness or range of thickness. Of course, the number of different thicknesses or ranges indicated could be more or less than four. The specific thicknesses or ranges corresponding to each of the different colors will be further detailed below.

FIG. 2F illustrates a subsequent step in the process of mapping the pericardial sac 50 in preparation for cutting heart of leaflets therefrom. Specifically, zones 80a, 80b, 80c are depicted corresponding to contiguous grid units 74 of the same or similar thickness. Each of the zones 80 is delineated by a zone border 82 and by a zone indicator 84. In the illustrated example, the zone indicators 84 are the letter symbols A–C corresponding to the three usable thicknesses.

Figure 3:
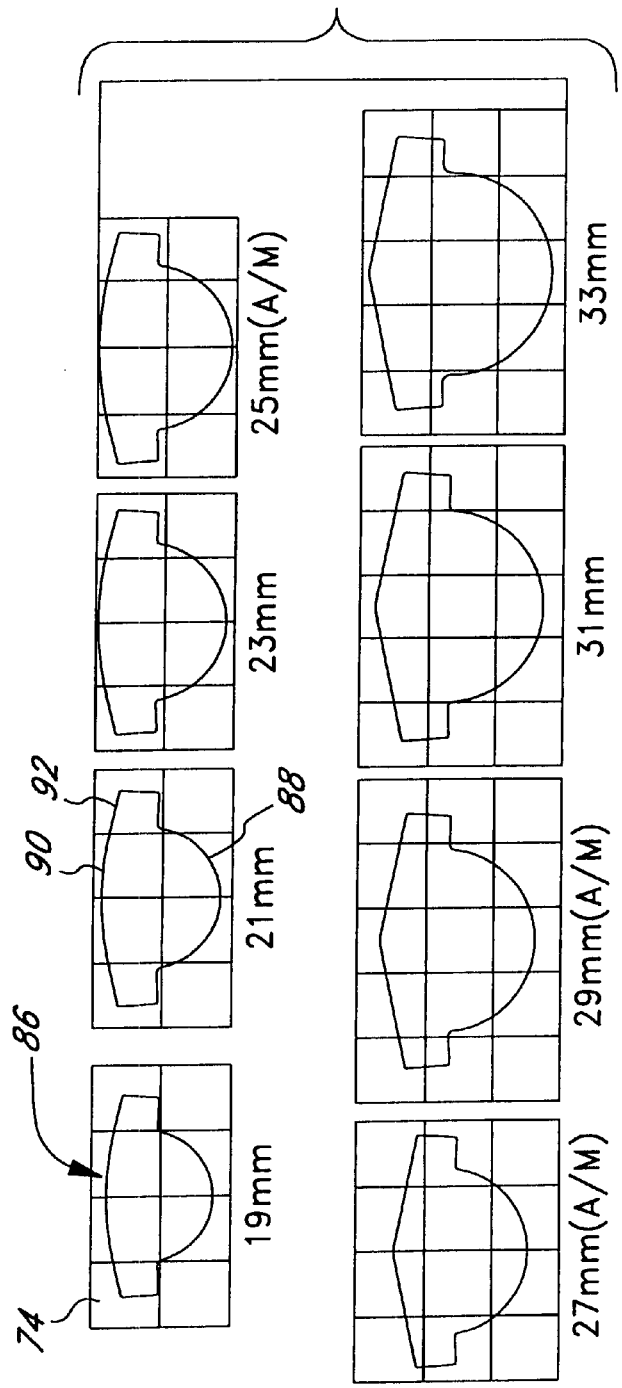
FIG. 3 shows a series of plan views of a number of sizes of heart valve leaflets with grid patterns used in the present invention superimposed thereover.

With reference to FIG. 3, a number of 2×4 or 4×5 arrays of grid units 74 are shown with the outlines 86 of various sizes of heart valve leaflets superimposed thereupon. Each leaflet outline 86 includes an arcuate cusp edge 88, a coapting edge 90, and a pair of oppositely-directed commissure tabs 92 separating the cusp and coapting edges.

These illustrations show how many grid units 74 are needed to form an area from which a particular size leaflet may be cut. For example, a 27 mm leaflet requires an area defined within a 4×5 array of grid units 74. Of course, as explained above, the size of the grid units 74 can be varied, and thus the number of grid units within each required array can be varied. In the present embodiment, each of the grid units 74 is a square with sides of about 9.5 mm (0.375 in.), and thus the array of grid units needed to form a 27 mm leaflet has size of about 38.0 mm×47.5 mm (1.5 in.×1.875 in.).

Figure 4:
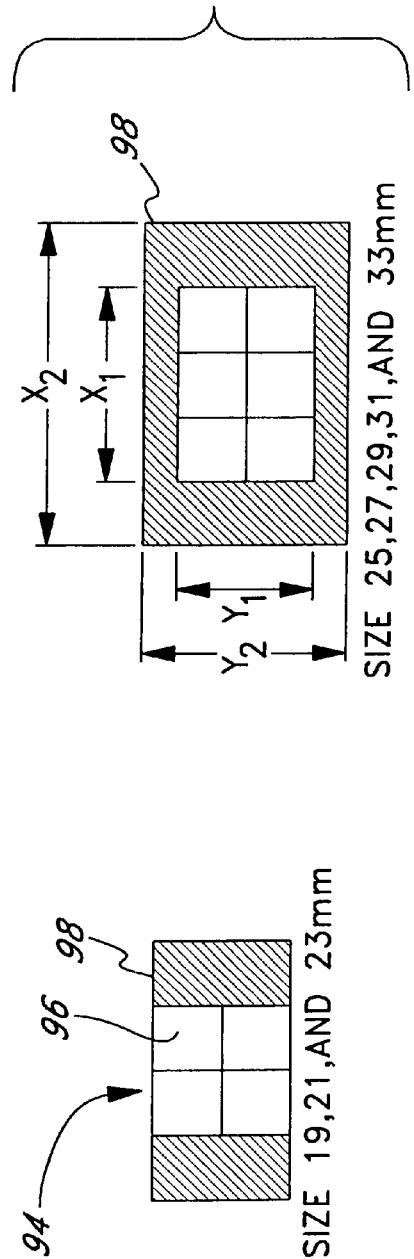
FIG. 4 shows three rectangular areas that are suitable for forming different sized leaflets.

The desired thickness of pericardium for heart valve leaflets varies with the size of the leaflets, with smaller leaflets generally being thinner than larger leaflets. Although the overall area on the pericardial sac 50 needed to cut a particular size leaflet is seen in FIG. 3, the entire area need not be the desired thickness of the leaflet. FIG. 4 illustrates preferred patterns 94 of pericardium from which to cut various sized leaflets. Specifically, the left pattern is for 19, 21, and 23 mm leaflets, and the right pattern is for 25, 27, 29, 31, and 33 mm leaflets. These patterns are derived by superimposing the leaflet shapes over the arrays of grid units as indicated in FIG. 3 and determining the size of the mid-portion of each leaflet relative to the respective array. It is believed that as long as the mid-portion of each leaflet is the desired thickness that it will perform adequately. That is, the mid-portion of each leaflet is generally defined by the area within the cusp edge 88 and by extension of the cusp edge to the coapting edge 90. The commissure tabs 92 are typically folded and sutured around structural commissure posts within the heart valve, and the thickness thereof is deemed less important.

An interior region 96 of each pattern 94 comprises a regular array of whole grid units 74, while a peripheral region 98 need not correspond to whole grid units. The interior region 96 has a thickness that corresponds to the preferred thickness of the particular leaflet being cut, while the thickness of the peripheral region 98 may or may not be the same thickness. The dimensions $x_1$, $x_2$, $y_1$, and $y_2$ for the interior regions 96 and overall pattern 94, are illustrated, and exemplary values are given below in TABLE I.

TABLE I

PREFERRED PATTERN DIMENSIONS FOR DIFFERENT SIZED LEAFLETS

| LEAFLET SIZE (mm) | THICKNESS RANGE OF INTERIOR REGION 96 mm, (inch) | THICKNESS RANGE OF PERIPHERAL REGION 98 mm, (inch) | $X_1$ mm, (inch) | $X_2$ mm, (inch) | $Y_1$ mm, (inch) | $Y_1$ mm, (inch) |
|---|---|---|---|---|---|---|
| 19, 21, 23 (Aortic) | 0.345–0.470, (.0136–.0185) | 0.318–0.648, (.0125–.0255) | 19.05, (0.75) | 38.1, (1.5) | 19.05, (0.75) | 19.05, (0.75) |
| 25, 27, 29 (Aortic and Mitral) | 0.447–0.546, (.0176–.0215) | 0.419–0.648, (.0165–.0255) | 28.58, (1.125) | 47.63, (1.875) | 19.05, (0.75) | 28.58, (1.125) |
| 31, 33 (Mitral) | 0.523–0.597, (.0206–.0235) | 0.495–0.648, (.0195–.0255) | 28.58, (1.125) | 47.63, (1.875) | 19.05, (0.75) | 28.58, (1.125) |

Exemplary Measuring and Mapping System

FIGS. 5, 6 and 7A–7C illustrate an exemplary automated system 100 for measuring, mapping, and marking a sheet of bio-material in accordance with the present invention. The system is designed to receive sheet-like bio-material in a variety of configurations, such as the flattened sac 50 seen in FIG. 2C, and output a sheet having specific markings thereon corresponding to the implant or prosthetic component being produced. Alternatively, as mentioned above, one or more of the measuring, mapping, and marking functions may be performed elsewhere either manually or with the assistance of a further automated mechanism.

Figure 6:
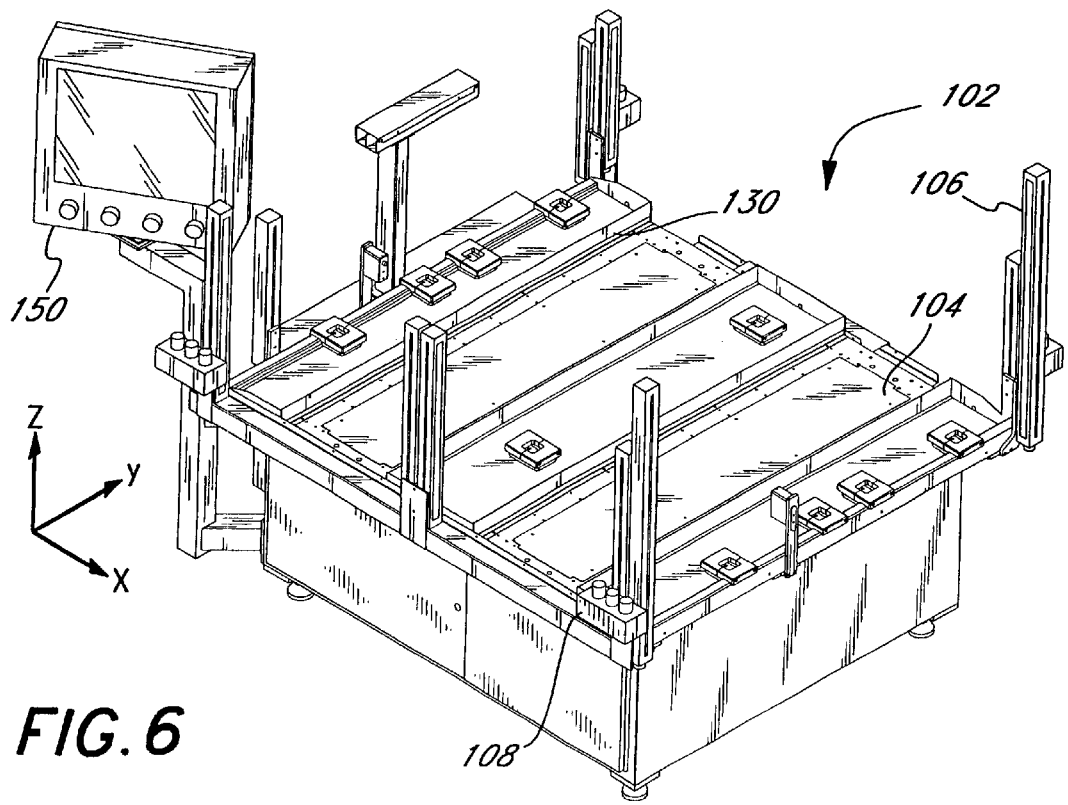
FIG. 6 is a perspective view of the apparatus of FIG. 5 with a number of upper components removed to illustrate a base portion.

The system 100 generally comprises a base 102 and a plurality of mechanical, electrical, and optical subsystems mounted thereon. The base 102 is a relatively sturdy rectilinear structure, and is illustrated separately in FIG. 6 with a number of operating components removed therefrom. The base 102 defines a horizontal table 104 over which the bio-material sheets translate and are measured. The table 104 is rectangular and a plurality of upstanding light curtain columns 106 are mounted at each corner, and at a midpoint along one side. The columns 106 generate planar optical safety curtains when the system 100 is in operation which, when broken, trigger an automatic shutoff function. In this manner, the system 100 will not operate when a user's hand is within the rectilinear volume defined within the columns 106. FIG. 6 also illustrates a plurality of on/off operating switches 108 conveniently disposed at each corner of the table 104. Finally, coordinate axes are shown in FIG. 6 corresponding to the three primary orthogonal directions. The two-dimensional illustrations of FIGS. 7A–7C also include their respective coordinate axes.

Figure 7A:
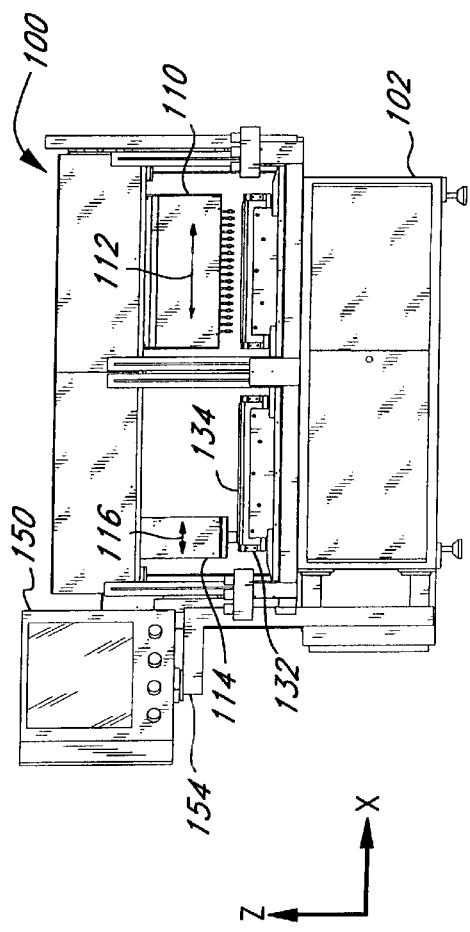
FIGS. 7A–7C are plan and elevational views of the apparatus of FIG. 5.
Figure 7C:
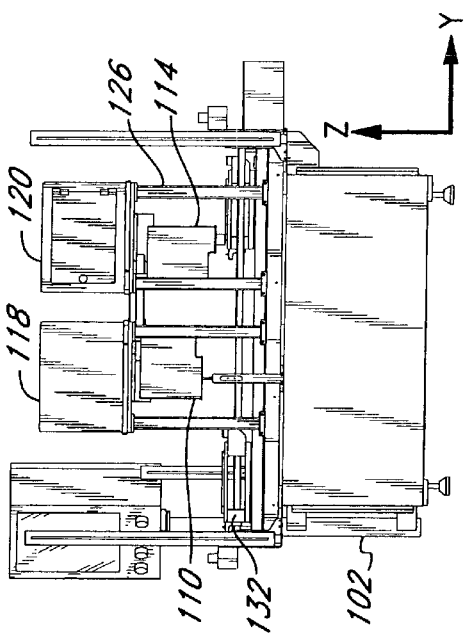

The system 100 has two main operating subsystems, a measurement subsystem and a marking subsystem. The measurement subsystem comprises a measurement head 110 supported to translate above the table 104 and along the X-axis, as indicated by the arrow 112 in FIG. 7A. The marking subsystem comprises a marking head 114 also supported to translate above the table 104 and along the X-axis, as indicated by the arrow 116. The respective mechanisms for supporting and linearly translating the measurement head 110 and marking head 114 are contained within housings 118, 120, as seen in FIGS. 7A and 7C. The mechanisms within the housings 118, 120 are not shown, and may take a number of conventional forms, including a preferred form of a linear slide and a motorized threaded rod combination. For example, a motor 122 shown in FIG. 7B projecting from the left side of the housing 118 has an output shaft that rotates about the X-axis and turns a threaded rod for translation of the measurement head 110. Likewise, a motor 124 extends from the left side of the housing 120 and turns a threaded rod to translate the marking head 114. The housings 118,120 are, in turn, supported above the table 104 on legs 126. The particular structure and functions of the measurement and marking subsystems will be described in more detail below.

Figure 7B:
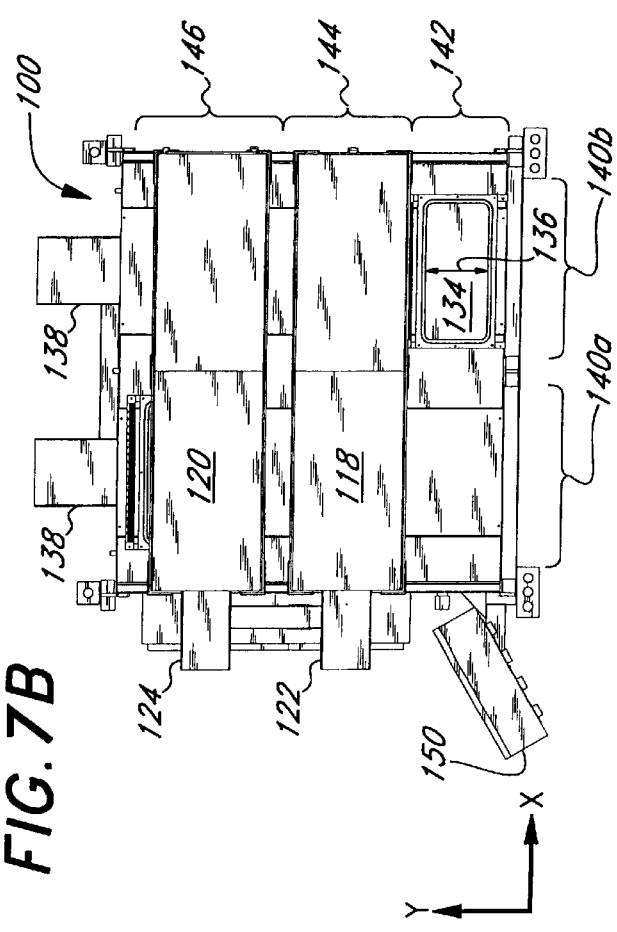

The table 104 includes a pair of channels 130 as seen in FIG. 6 extending from one edge to the other of the table along the Y-axis. The channels 130 receive mechanisms for linear translation of a pair of workstations or carriages 132, which are described in detail below with respect to FIGS. 10 and 11. The carriages 132 each defined thereon a work surface 134 that serves as a work platform for measuring the thickness of the bio-material sheet. FIG. 7B illustrates one of the work surfaces 134 and its direction of movement 136 along the Y-axis. Again, the mechanisms for translation of the carriages 132 are not shown, although a preferred form includes a linear slide and motorized threaded rod combination. In this regard, a pair of motors 138 are shown projecting from the side of the base 102, which motors include output shafts that rotate about the Y-axis and turn threaded rods for translation of the carriages 132.

With reference now to the plan view of FIG. 7B, a first track 140a and a second track 140b are defined, respectively, for the two carriages 132 along the extent of their travel in the Y-axis. Both tracks 140a, 140b extend the entire width of the table 104 and intersect three distinct workstations. Specifically, a load station 142 is defined at the lower portion of FIG. 7B by a portion of the table 104 that is exposed from underneath either housing 118 or 120. In addition, a measurement station 144 is defined below the measurement head 110, and a marking station 146 is defined below the marking head 114, for each track 140. The carriages 132 shuttle along their respective tracks 140a, 140b from the load station 142 to the measurement station 144, from there to the marking station 146, and then back to the load station.

The various subsystems of the automated system 100 are actuated, monitored and coordinated through a programmable controller, as will be more fully explained below. Various inputs to the controller are supplied via a human-machine interface 150, which in the illustrated embodiment comprises a computer monitor having a touch screen 152. The monitor 150 is conveniently mounted on a stanchion 154 at one corner of the base 102.

Figure 8:
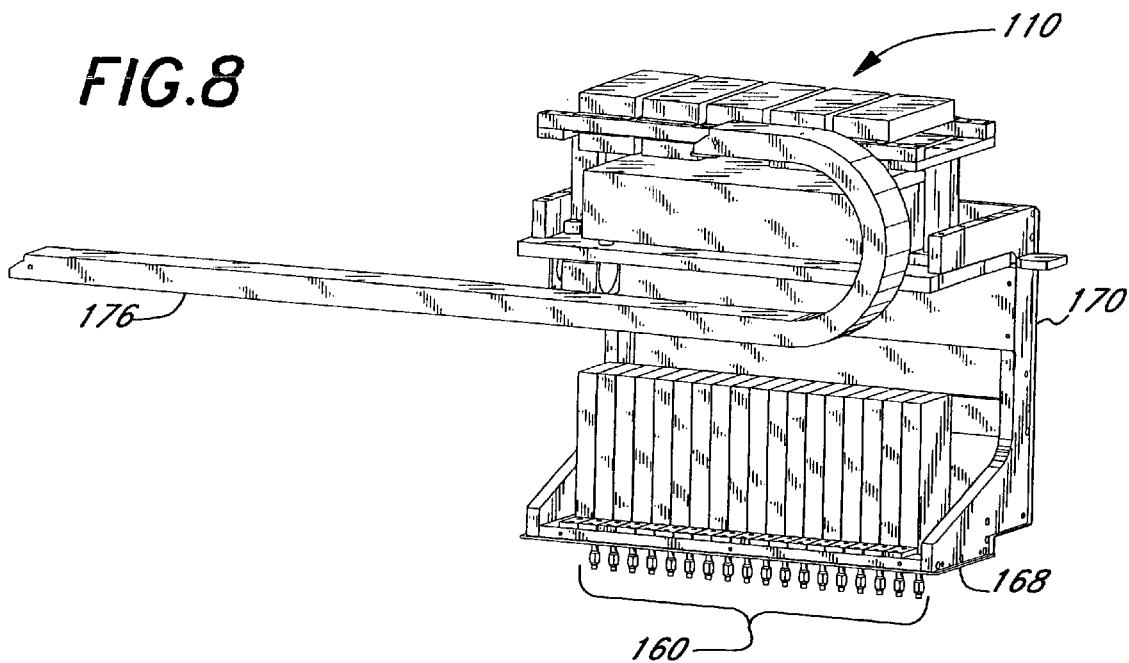
FIG. 8 is a perspective view of an exemplary thickness measuring tool used in the apparatus of FIG. 5.
Figure 9A:
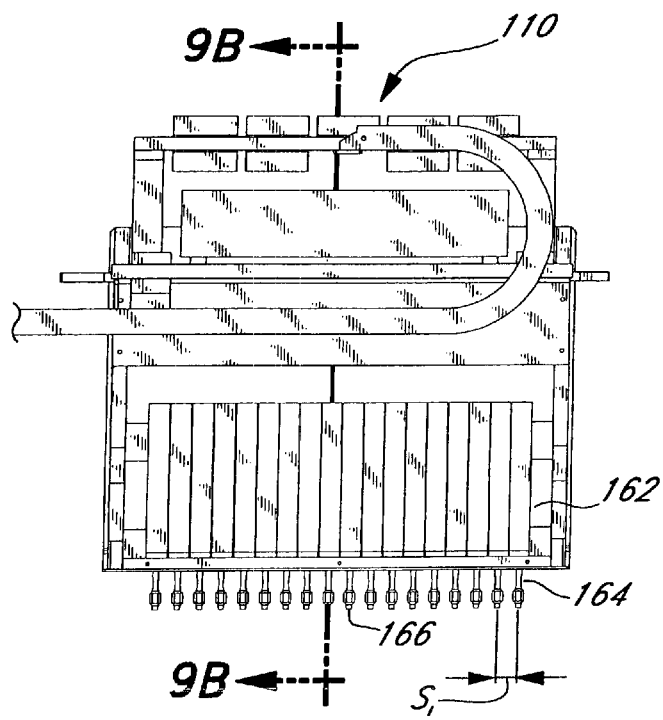
FIGS. 9A–9B are front and side elevational views, respectively, of the thickness measuring tool of FIG. 8.
Figure 9B:
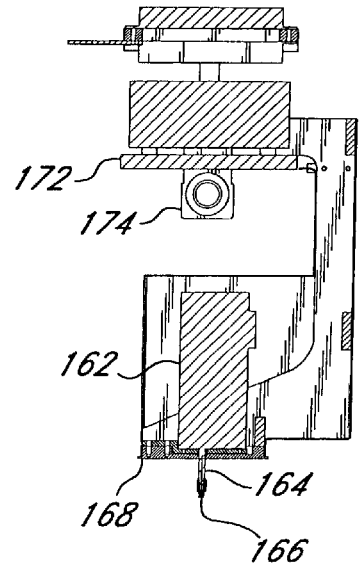

FIGS. 8 and 9A–9B illustrate various details of the measurement head 110 of the present invention. The operational portion of the measurement head 110 comprises a plurality of sensors 160 arrayed in a line and directed downward in the Z-axis. The sensors 160 may take a variety of forms, but can generally be categorized into those sensors that contact the bio-material and those that do not. That is, contact sensors are designed to produce a signal upon contact with the bio-material that, in combination with knowledge of the relative height of the sensor above the work surface 134, produces the thickness of the bio-material. Non-contact sensors, such as infrared or laser sensors, emit an electromagnetic wave or optical beam toward the bio-material and detect the thickness thereof from the reflected wave or beam. The present invention encompasses any sensor that can detect the thickness of a material relative to a reference surface on which the material is placed.

In a presently preferred embodiment of the invention, the sensors 160 comprise linear actuators 162 that displace a shaft 164 having a tip 166 into contact with the bio-material. With knowledge of the position of the shaft 164 upon contact of the tip 166 with the bio-material, the linear actuator produces an electronic signal corresponding to the thickness of the bio-material at that point. The linear actuators 162 are supported on a platform 168 having apertures therethrough for the shafts 164. The platform 168 is suspended on a frame 170 underneath a mechanism for translating the measurement head 110. Specifically, a slide plate 172 is adapted to translate within a corresponding groove (not shown) fixed with respect to the base 102 and an internally threaded screw block 174 travels along the aforementioned motorized threaded rod actuated by the motor 122 (FIG. 7B). The moving measurement head 110 communicates with the rest of the system 100 via a cable carrier 176, or similar expedient.

As mentioned, the sensors 160 are aligned in a linear array in parallel with the X-axis to form a row of sensors. Desirably, there are at least two sensors 160 to speed up the measurement and mapping function of the system 100, and preferably there are at least three sensors, with at least ten being most preferred. The illustrated embodiment includes eighteen sensors 160 spaced apart a distance $S_1$. In this configuration, therefore, eighteen separate points on a bio-material spaced apart a distance $S_1$ can be simultaneously measured by the measurement head 110 (a row of measurements). As will be explained below, relative displacement between the bio-material and the measurement head 110 in the Y-axis enables measurement of a second row and subsequent rows of eighteen points, which results in a two-dimensional array of thickness measurements. Each sensor 160 thus measures a column of points in the Y-direction.

The distance $S_1$ between the sensors 160 may be equal to or greater than the center-to-center spacing S of the grid units 68 in the grid pattern 66 shown in FIG. 2D. Desirably, the distance $S_1$ is an even multiple of the spacing S so that more than one column of measurements along the Y-axis is made, each column being offset from the adjacent column by the grid spacing S. In a preferred embodiment, the distance $S_1$ is 28.6 mm (1.125 in) and the spacing S is 9.5 mm (0.375 in), so that three columns of offset measurements are made.

Of course, other arrangements of sensors 160 may be used to produce a two-dimensional array of thickness measurements. For instance, the relative displacement between the measurement head 110 and the bio-material may be other than linear as disclosed herein, such as rotational. Alternatively, the sensors 160 may be arranged in a two-dimensional array, as opposed to being in line. In the latter arrangement, a single measurement taken by the measurement head results in a two-dimensional array. Those of skill in the art will therefore understand that there are variety of sensor configurations and measurement techniques within the scope of the present invention for producing a two-dimensional array of thickness measurements.

It should also be noted at this point that although the system 100 is illustrated as being especially suitable for measuring and mapping a planar sheet of bio-material, it is contemplated that the bio-material may be other than planar, such as tubular. Also, in this respect, the term "flatten" the sheet on the work surface should not be construed to imply a planar work surface. As an example of an other than planar work surface, the tubular bio-material may be mounted on a cylindrical mandrel with the measurement head 110 adapted to rotate therearound to measure the thickness of the tube and produce a three-dimensional topographical map. Likewise, mapping of bioprosthetic surfaces that are defined on three-dimensional objects other than sheet substrates is also possible with modification of the apparatus of the present invention. For example, the free-sliding pin type of sensor may be used to accurately measure more pronounced topographical changes, much like the familiar desktop novelty having an array of free-sliding pins mounted in a frame. In short, other arrangements are possible, and the invention should not be considered limited to measuring planar or even sheet substrates.

FIGS. 10 and 11A–11B illustrate details of the carriage 132 of the present invention for supporting the sheet-like bio-material, such as a flattened bovine pericardium sac 180. The carriage 132 comprises a generally hollow frame 182 supporting a rectilinear platen 184 thereon. The upper surface of the platen 184 defines the work surface 134 previously mentioned. The work surface 134 on which the sheet-like bio-material is measured is microbiologically clean and sanitary to inhibit contamination of the material. The sheet-like bio-material may be clamped to the surface 134 to prevent movement using conventional clamps (not shown), but in a preferred embodiment, the bio-material is simply laid flat on the surface and smoothed down with a wiper device, such as a rubber squeegee-like device. If bovine pericardium is used, it has been found that the wiping method works adequately, which reduces the setup time and equipment needed, and also reduces the foreign surfaces contacting the pericardium.

An internally threaded screw block 186 is seen underneath the frame 182 in FIG. 11B, which block travels along a motorized threaded rod driven by one of the motors 138 (FIG. 7B). A calibration bar 188 is secured at one side of the frame 182 and is generally aligned along the X-axis. The calibration bar 188 includes a number of stepped calibration surfaces 190, also extending along the X-axis. The calibration surfaces 190 provide precision measurements for the sensors 160 during a calibration process. That is, a series of surfaces 190, including a zero reference surface, having known relative elevations is provided on the calibration bar 188. The elevation values of the surfaces as measured by the array of sensors 160 permits the user and/or system to detect any non-calibrated or otherwise faulty sensors. If such a condition exists, the faulty sensor may be reprogrammed, repaired to replace a malfunctioning part, or replaced altogether.

The X-axis and Y-axis are indicated in the plan view of FIG. 11A. The bovine pericardium sac 180 is shown oriented with the base-apex line 192 parallel to the X-axis. In this manner, the sac 180 is desirably be measured, mapped, and then marked in a grid pattern that is either parallel to or perpendicular to the base-apex line 192. Because the fiber orientation of the sac 180 is generally known with respect to the base-apex line 192, cutting the individual heart valve leaflets with respect to the marked grid pattern is facilitated.

FIG. 12 illustrates a tip cleaning tray 194 and associated tip cleaning cover 196. A pair of end mounts 198 permit the cleaning tray 194 to be secured with respect to the carriage 132 for cleaning the tips 66 of the sensors 160. That is, each tip 166 extends through an aperture in the cover 196 into a cleaning solution provided within the tray 194. A preferred cleaning regimen will be described below.

Electrical Component Interfaces

FIG. 13 schematically illustrates the main electrical components of the system 100 of present invention, and their interconnections. The system 100 is controlled primarily through a programmable logic controller (PLC) 200 that transfers information back and forth to a human-machine interface 202 through an ethernet connection 204. The human-machine interface 202, in turn, communicates with a plurality of measurement sensors within a measurement head 206. Specifically, a communication line 208 (denoted COM1) from the human-machine interface 202 connects directly to a code operated switch (COS) 210, which connects via a plurality of RS 232 cables 212 to each sensor within the measurement head 206. A digital input/output (I/O) cable 214 transfers information to and from the PLC 200 and a marking head 216. One or more remote input/output (I/O) cables 218 transfer information to and from the PLC 200 and a plurality of servo drives 220 used to translate the measurement head 206, marking head 216, and workpiece carriages (not shown in FIG. 13). A digital input/output (I/O) cable 222 transfers information to and from the servo drives 220 and the marking head 216 to turn on and off the ink jet.

Specific examples of these various electrical components will now be given, with the understanding that alternative equipment and/or manufacturers could be substituted. The programmable logic controller 200 may be an Allen Bradley 5/40E (series 5 model 40) with an ethernet port. The HMI 202 may include an IBM-compatible computer and a Christensen 18 inch touch-screen monitor model number LSX18T, with ELO touch screen software. The code operated switch (COS) 210 is available from Black Box Corp., of Lawrence, Pa. That has 16 serial input communication ports and 1 serial output port connected to the HMI 202. The sensors 160 within the measurement head 206 are desirably servo feedback displacement actuators, such as are available from SMAC (Carlsbad, Calif.) as model LAL-37-050-50-DC-MOD, and controlled by SMAC model LAC-25 two-axis controllers, or their equivalent. The marking head 216 desirably comprises a BioDot (Irvine, Calif.) ink jet marking pen having a dispensing platform model BioJet Quanti 3000 and a dispensing head model BioJet BLJ4000. The "ink" dispensed is desirably a toxicity-free reagent or dye. The servo drives that control movement of the workpiece carriages, the sensors within the measurement head 206, and the marking head 216, are desirably made by Allen Bradley of Milwaukee, Wis., and include model 1326AB-B410G-21 servo motors. The system 100 is supplied with 480 volts from the power grid for the servo drives 220, which power is transformed to 120 volts for those components, including the PLC 200, requiring such standard power supply. The sensors within the measurement head 206 may require DC power, and thus 24 volt DC power supplies may be provided.

The HMI 202 desirably includes a touch-screen monitor that is mounted directly to the physical components of the system 100, as explained above. This configuration enables close monitoring of the system and rapid modification to the operation thereof by a user having a first-hand view. The touch-screen monitor is relatively more sanitary than, say, a keyboard, and is thus preferred for clean manufacturing practices. However, the HMI 202 could be located outside a "clean room" in which the physical components of the system are placed, and thus could take the form of a number of such interfaces.

Various software applications are preferably utilized in conjunction with the aforementioned electrical components to operate, monitor, and coordinate the various system actions. For example, the HMI 202 desirably includes a supervisory, control, and data acquisition (SCADA) software package that uses Visual Basic in the background and for configuration, such as a program sold under the brand-name Fix Dynamics from Intellution of Norwood, Mass. The relay ladder logic of the controller 200 controls the general machine functions, including receiving commands from the HMI 202 concerning when and where to move the servo drives 220, checking the safety conditions, relaying the movement information to the servo drives 220, and telling the marking head 216 when and where to dispense dye. The preferred Allen Bradley servo drives 220 are programmed using GML software from Allen Bradley. Logic associated with the marking head 216 is pre-programmed with a dye pump speed to assure that the dye supply will not run out during any marking cycle.

The preferred sensors within the measurement head 206 include a linear actuator and a controller. Each controller may be associated with one or more linear actuators, typically two. Therefore, in the preferred embodiment illustrated above, there are 18 linear actuators and 9 controllers. Each controller is programmable, preferably via the HMI 202. In the exemplary embodiment, the SMAC linear actuators and controllers permit the position, speed, acceleration, torque and force of a coil-driven shaft to be programmed.

There are four programs associated with the servo drives 220. One program is associated with the movement of each of the workpiece carriages 132, a third program is associated with movement of the measurement head 206, and a fourth program is associated with movement of the marking head 216. Again, each of these programs is adjustable using the Allen Bradley GML software, preferably via a laptop computer.

The exemplary marking head 216 is also programmable, although the program is edited using a BioDot hand-held terminal. Once edited, however, the marking head 216 program may be downloaded to a personal-computer as a backup.

Overall Pericardial Tissue Processing and Measurement

In the present invention, the pericardial sac 50 is desirably fixed with a buffered solution of glutaraldehyde or other fixative. After fixation, the sac 50 is quarantined and then cleaned prior to the thickness measurement as described herein. The thickness of the entire tissue surface of the sac 50, or portion thereof, is automatically measured at a resolution of $\frac{3}{8}$ inches center-to-center and mapped. Data from these measurements is then used to generate a complete tissue thickness mapping profile. The thickness map is used to identify and mark tissue thickness areas or tissues zones from which to cut leaflets. The marked tissue zones will be manually cut out and sorted per thickness ranges. The tissue zones will be visually inspected per bio-sort criteria before transferring to a cutting operation where acceptable tissue areas will be manually die cut into leaflets. In an alternative sequence, the quarantine step occurs after the measurement, mapping, marking, and cutting steps.

Measuring and Mapping Operation

An example sequence includes:

1. Load bio-material sheet onto first measurement platen corresponding to first workpiece track;
2. Initiate measurement/marking cycle by pushing start button;
3. Advance platen in Y-direction along first workpiece track to measurement station;
4. Translate measurement head in X-direction to position sensor array above platen in first workpiece track;
5. Contact sensor array to top surface of bio-material sheet with controlled light force to measure a row of points;
6. Transfer data corresponding to thickness of bio-material sheet to control system;
7. Advance platen in Y-direction and measure another row of points;
8. Repeat steps 5–7 until the bio-material sheet has been measured along the Y-direction;
9. Optionally, offset measurement head in X-direction and repeat steps 5–8 to obtain a grid of measurements;
10. Generate a thickness map using the software algorithm in the control system;
11. Advance platen in Y-direction along first workpiece track to marking station;
12. Translate both measurement head and the marking head in the X-direction so as to switch places above workpiece tracks, with marking head positioned above platen in first workpiece track;
13. Mark bio-material sheet on platen in first workpiece track into thickness zones using marking head and thickness map instructions from control system;
14. Advance platen in first workpiece track in Y-direction to load station to enable removal of the measured and marked bio-material sheet.

The above sequence corresponds to the measurement marking of a bio-material sheet on one of the platens and workpiece tracks in the system of the present invention. As described above, however, there are desirably two platens and workpiece tracks operating in parallel. Therefore, the following general sequence may also be followed to increase throughput of the system:

1. Load sheet on platen 1 and translate along track 1 to measurement station;
2. Measure and map sheet on platen 1;
3. Translate platen 1 to marking station;
4. Translate measurement head over track 2;
5. Load sheet on platen 2 and translate along track 2 to measurement station;
6. Simultaneously measure and map sheet on platen 2 while marking sheet on platen 1;
7. Translate platen 1 to load station and remove sheet;
8. Translate platen 2 to marking station;
9. Map sheet on platen 2;
10. Translate platen 2 to load station and remove sheet.

Thickness Measurement Alternatives

As mentioned above, various means can be used to measure the thickness of bio-material sheet in accordance with the present invention. If a contact measurement method is used, the following parameters are preferred;

a sampling increment center-to-center distance of 9.5 mm (0.375 inches)

a flat contact tip of a diameter of approximately 7.0 mm (0.275 inches)

a vertical measuring force equivalent to the force applied by a Mitutoyo low-pressure model 543 measurement gauge; i.e., with the spring attached and the weight removed, a force of less than 0.42 N or 43 g a measurement table dimension in the X-Y plane of 8 inches by 20 inches a linear actuator accuracy of about 0.013 mm (0.0005 inches) or less an X-Y positioning accuracy of about 0.13 mm (0.005 inches) or less scan time for thickness measurement of a pericardial sac of 2 minutes or less a range of sheet thickness measurements of 0.356–0.584 mm (0.014–0.023 inches)

Other non-contact measurement approaches include laser or ultrasound scanning. For best results using such devices, extensive testing should be undertaken to determine the level of accuracy, repeatability, and reliability. Laser scanning in particular offers the advantages of being faster and cleaner than contact methods. In addition, a laser scanner has a relatively simple moving mechanism and can be purchased at a reasonable cost. Unfortunately, a laser will be more sensitive to vibration, moisture, surrounding lighting, surface finish condition, and dust/particles in the air.

One specific example of the use of lasers is in conjunction with free-sliding pins. The pins contact the top surface of the sheet being measured and a laser measures the locations of the tops of the pins. Another contact-type measurement system utilizes a multi-axis servo controller encoder from Axima. The measurements involve using free-sliding pins to touch the bio-material sheet while the position of each pin is determined by the encoder. The positions of the pins may be monitored by pairs of photo or smart fiber-optic sensors which provides small beams in a range of 0.002–0.004 mm with low hysteresis for quick detection. The photo eyes are constantly monitored by the controller through programmable control logic for break continuity. The position of the pins is determined by the count or number of turns of the built-in encoder. The pin height accuracy of the Axima encoder is in the range of 0.0076 mm (0.0003 inches).

Marking Method Preferences

The system 100 maps and then marks the zones 80a, 80b, 80c depicted in FIG. 2F corresponding to contiguous grid units 74 of the same or similar thickness. As mentioned elsewhere herein, the zones are desirably cut out, inspected, and sorted, and leaflets are then cut from the zones using templates, or a similar expedient. Of course, it is also possible to mark not just the zones 80 with the system 100, but also the leaflet shapes themselves.

A non-contact printing method is desirably used for marking the bio-compatible sheet. In a preferred embodiment, the non-contact marking system is a high-performance dispenser utilizing ink jet technology and a toxicity-free reagent or dye. The marking system is constructed from stainless-steel, PTFE, and similar materials for corrosion resistance and biological compatibility.

Monitoring and Control Screens

Figure 5:
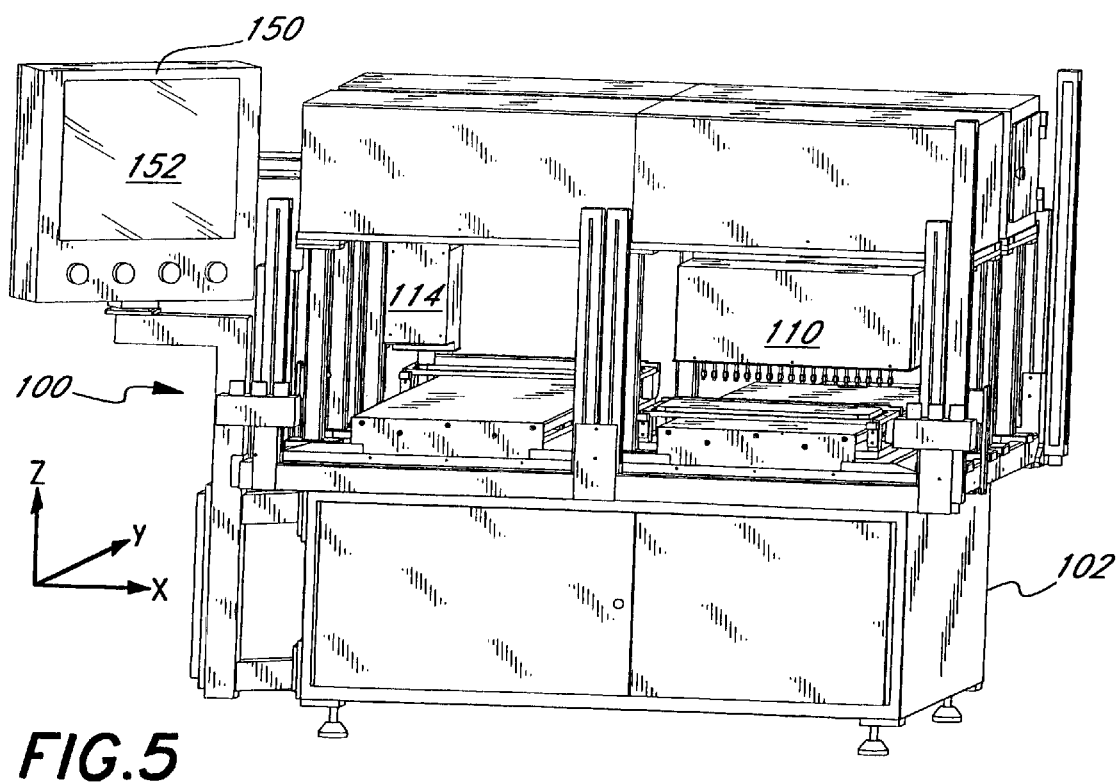
FIG. 5 is a perspective view of an apparatus of the present invention for measuring and mapping the thickness of sheet-like bio-materials.
Figure 14:
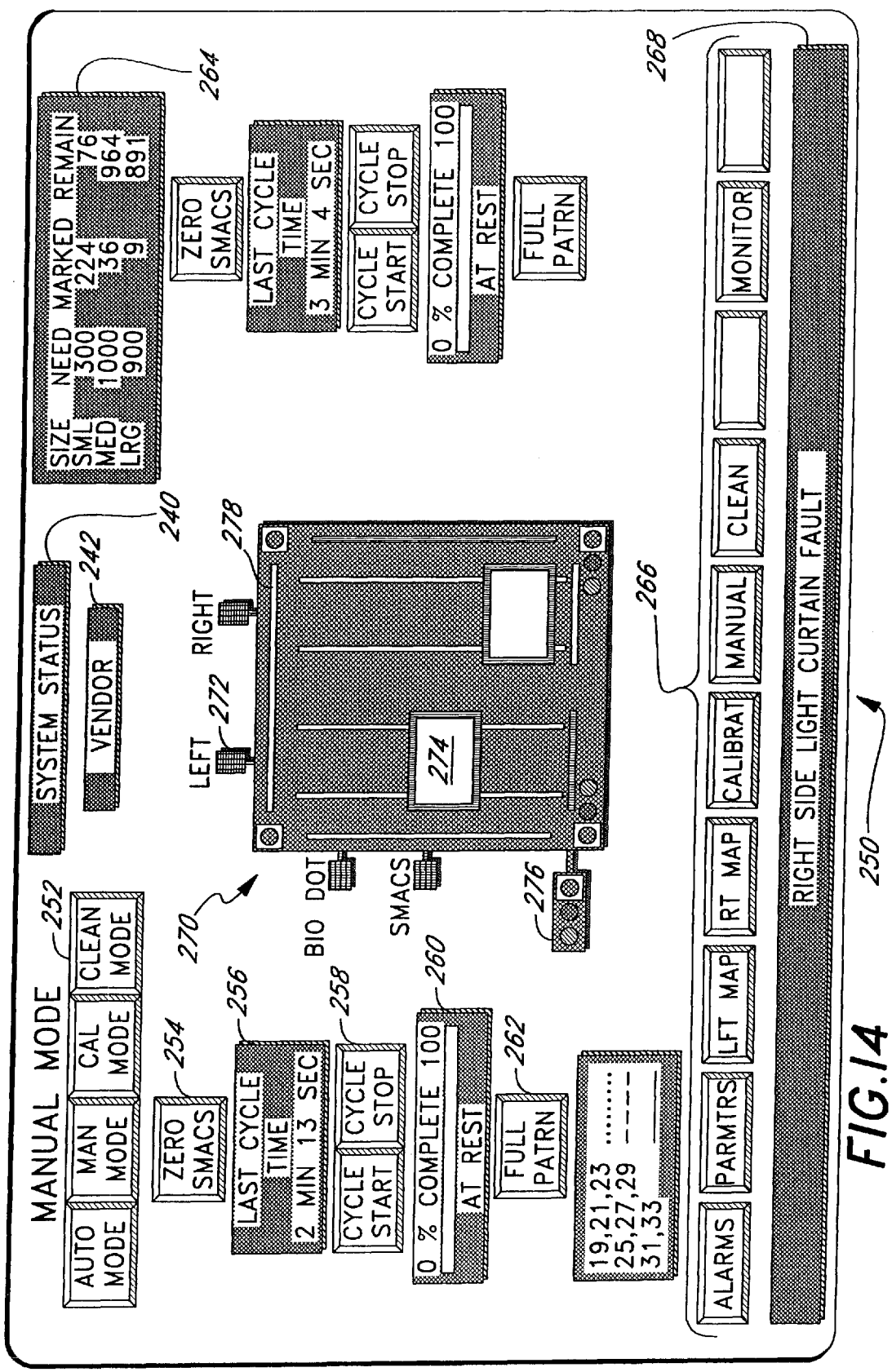
FIG. 14 is an image of the main touch screen display for use in operating the apparatus of the present invention.
Figure 15:
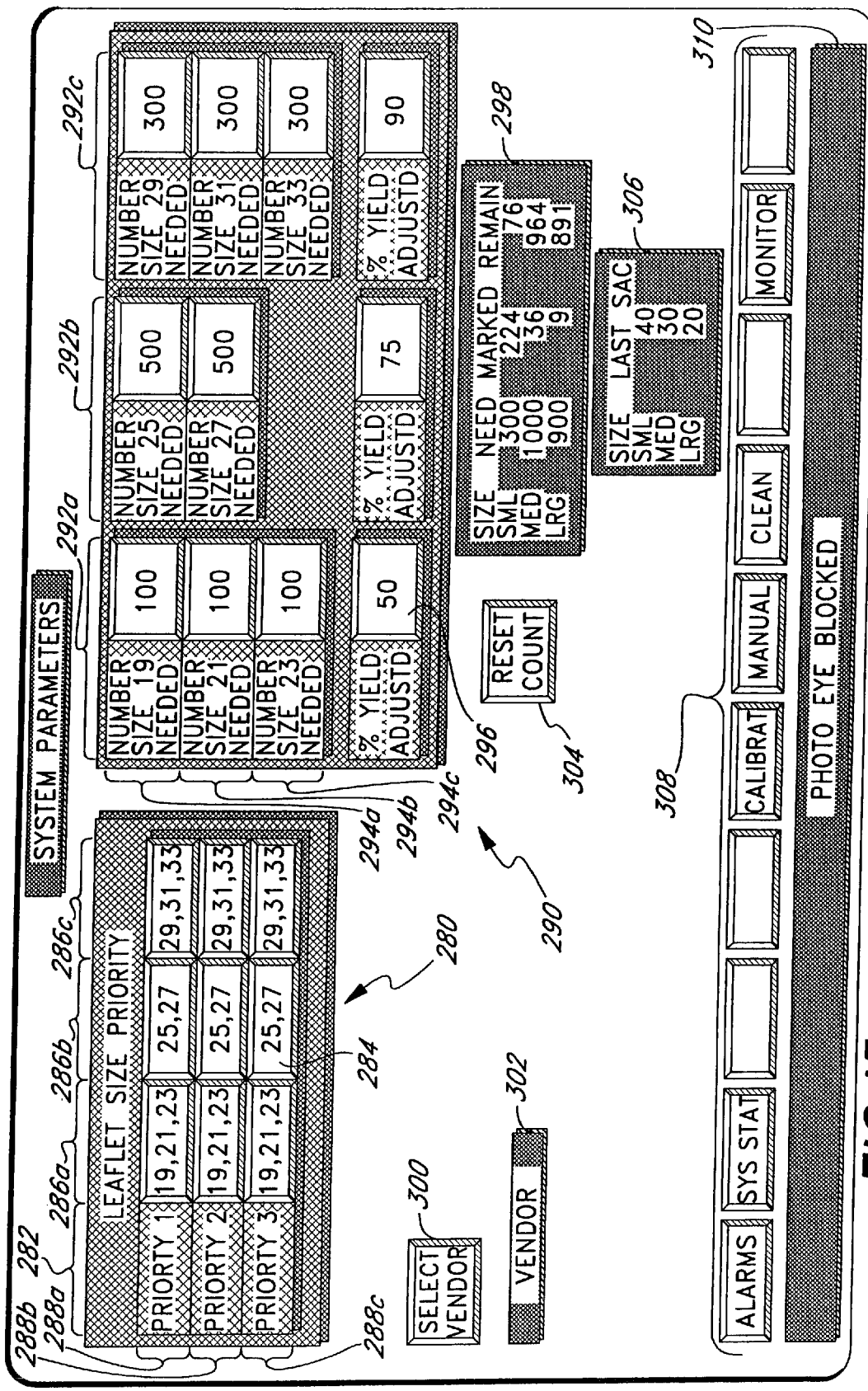
FIG. 15 is an image of a touch screen display for optimizing the tissue mapping function of the apparatus of the present invention.
Figure 16:
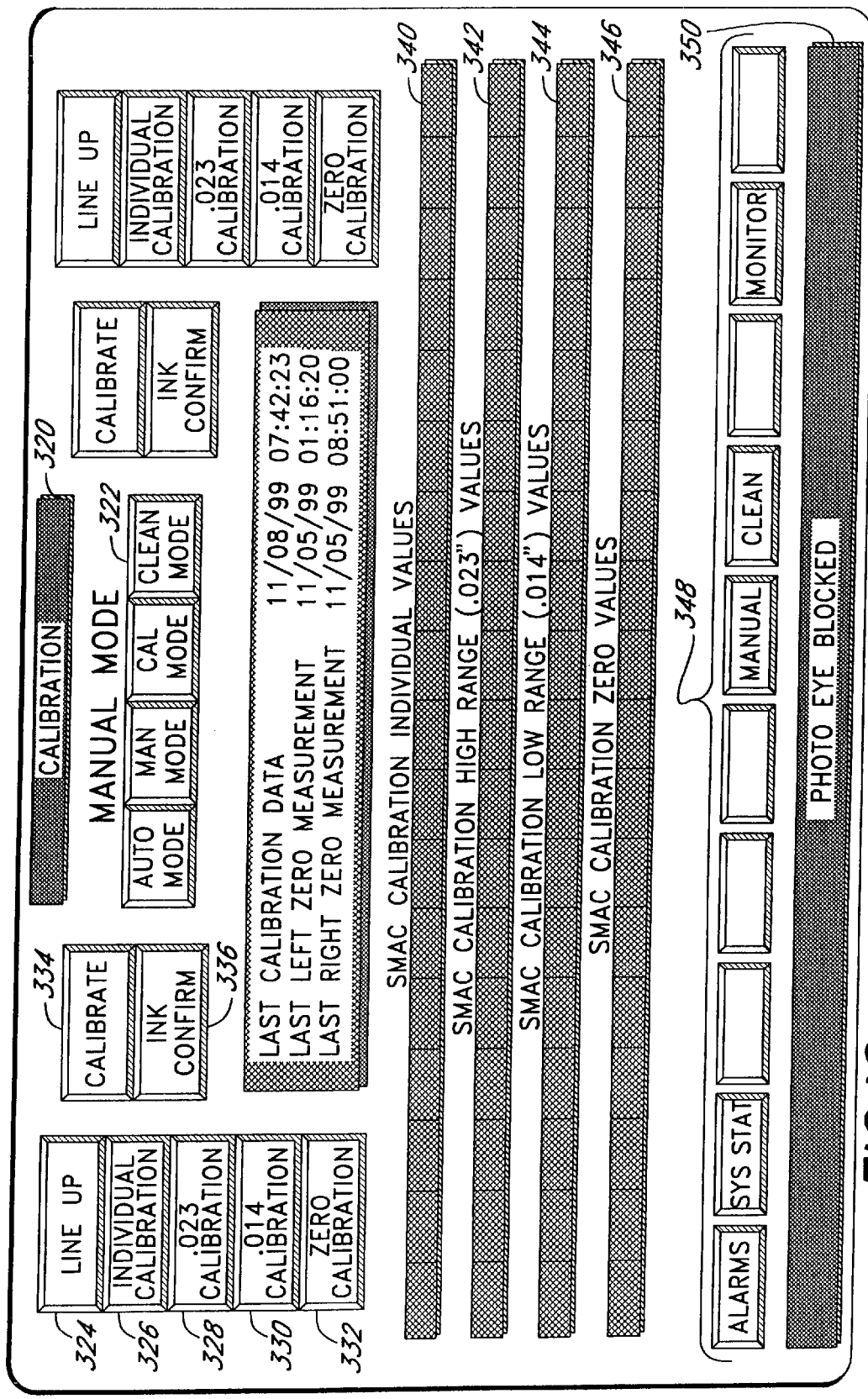
FIG. 16 is an image of a touch screen display for calibrating the apparatus of the present invention.

FIGS. 14–16 depict several images of an operator monitor and control screen, such as the touch-screen 152 seen in FIG. 5. Although the preferred embodiment utilizes touch-screen technology, the images in FIGS. 14–16 may be solely for monitoring purposes, with the actual control being accomplished via a different or remote device (i.e. a keyboard).

FIG. 14 illustrates a system status screen 250 that will be displayed during a majority of the operating sequence of the system 100. In effect, the system status screen is the default. The name of the particular screen is indicated in the middle top portion thereof, as seen in the display window 240. Just below the screen name 240, a display 242 indicates the particular vendor of the biocompatible sheet being measured and mapped (important for regulatory purposes when biological material is the workpiece).

In the upper left corner, the system status screen includes four mode buttons 252 providing overall control of the operating mode of the equipment. The four operating modes correspond to an automatic mode, a manual mode, a calibration mode, and a clean mode. It should be noted that each of the mode buttons 252, and indeed all of the various screen buttons, is a bordered icon to indicate its function as a button, with the ability to switch the button ON and OFF. Only one of the mode buttons 252 can be ON at one time, with the corresponding border typically being illuminated or colored differently to indicate its status in contrast with the other three buttons which are OFF. In addition, the particular mode selected is preferably indicated in textual form, as shown above the buttons 252 with the example "MANUAL MODE."

The operator typically actuates the calibration mode button prior to a production run, or at convenient intervals thoughout a run. A calibration sequence wherein each of the sensors 160 is calibrated against the calibration bar 188 will be described in more detail below.

It should be noted here that the status screen 250 duplicates a number of buttons and displays on the left and right side corresponding to the two workpiece carriages 132, beginning with a zero platen position button 254 entitled "ZERO SMACS," located just below the mode buttons 252, and continuing downward to a full pattern button 262. Therefore, the separate carriages can be monitored and controlled in parallel.

The zero platen position button 254 establishes a zero reference position of the sensors 160 against the work surface 134, from which sheet thickness measurements are taken. (The acronym "SMACS" refers to a particular vendor for the measurement sensors 160). That is, the operator presses the button 254 which causes the array of sensors 160 to contact the work surface 134 at multiple locations to establish a 2-dimesional array of reference heights across the platen 134. Typically, the platen 134 will be precision surfaced, but minor irregularities may exist or develop over time.

The display box 256 indicates the length of the last cycle for the respective left and right carriages 132. The length of the cycle generally corresponds to the size of the workpiece, and whether the full pattern button 262 has been actuated. Cycle start and stop buttons 258 function as toggle switches, and duplicate functions of the physical operator control buttons 108 provided at the corners of the table 104, as seen in FIG. 6. A display 260 indicates the percent completion of the current cycle for the two carriages 132.

The full pattern button 262, when actuated, programs the system 100 to read a full pattern covering the entire work surface 134 regardless of the actual workpiece size. At times it may be necessary to measure more than one sheet on the platen 134, and thus there may be irregular spaces between the sheets. The full pattern button 262 prevents the control system from prematurely discontinuing the measurement process, which otherwise occurs if the button 262 is not actuated and no sheet is sensed. In the normal situation, where only one relatively cohesively shaped sheet is being measured, the full pattern button 262 is not actuated. In that instance, the system 100 will measure a partial platen pattern; that is, the system will take measurements until all of the sheet on the work surface 134 has been measured and then stop. Specifically, the platen 134 translates in the Y-direction under the measurement head until all of the sensors 160 read zero elevation from the platen height (on the first pass, two additional zero measurements beyond the edge of the sheet are required to ensure the edge of the sheet has been reached).

In the upper right portion of the screen 250, a production requirements display 264 indicates the number of leaflets needed in each size (small, medium, or large), the number already mapped and marked, and, after a subtraction operation, the number of leaflets that remain to be mapped and marked. This display is important in keeping the operator apprised of the size of leaflet needed so that the system can be programmed to favor a particular size of leaflet.

Towards the bottom of screen 250, a series of navigational buttons 266 enable access to other screens in the program. As will be seen in FIGS. 15 and 16, the system status screen 250 appears as one of these navigational buttons 266. Again, these buttons 266 toggle one another so that only one can be actuated at any one time. Below the navigational buttons 266, a fault display 268 is provided along the entire bottom portion of the screen 250. The fault display 268 indicates the most recent alarm condition. Desirably, only those alarm conditions requiring immediate attention to continue production are displayed. In FIG. 14, the fault display 268 indicates that the right side light curtain has failed, which is a serious condition requiring immediate attention.

In the center of the system status screen 250, a schematic plan view 270 of the moving parts of the system 100 is displayed. The plan view 270 indicates, at 272, the operational status of each of the servo drives, including the two servo drives for the parallel carriages 132, a servo drive for the movement of the measurement head 110 (indicated as SMACS), and a servo drive for the movement of the marking head 114 (indicated as BIO DOT, which is a particular vendor for the marking head). The position of each of the carriages 132 is indicated at 274. The cumulative status of the four ON/OFF switches 108 around the table 104 is indicated at 276. That is, the indicator 276 will only illuminate the green light if all four of the ON/OFF switches 108 are in the ON position. Finally, a series of bars 278 around the periphery of the plan view 270 display the operational status of the light curtains around the physical system 100.

Prior to describing the system parameter screen shown in FIG. 15, the reader is referred back to the navigational buttons 266 in FIG. 14 in which the second button from the left selects the system parameter screen. In an exemplary embodiment of the present invention, wherein the system 100 is utilized for measuring and mapping biocompatible sheet for use in heart valve leaflets, a leaflet thickness priority display and control table 280 is provided in the upper left corner of the parameter screen. The table 280 includes a left column 282 that displays a series of priorities. A number of buttons 284 in the right three columns 286*a*, 286*b*, 286*c* can be actuated to order the leaflet thickness priority. The three primary choices in the left column 282 correspond to three rows 288*a*, 288*b*, 288*c* in the table 280. Because of their toggling relationship, only one button 284 in each column 286, and only one button in each row 288 can be actuated at any one time.

In the illustrated embodiment, the leaflet sizes (generally corresponding to leaflet thickness) are grouped into small (19, 21, and 23 mm), medium (25 and 27 mm), and large (29, 31, and 33 mm). Therefore, based on the initial production requirements, as modified during a production cycle and indicated in the display box 264 in FIG. 14, the operator can favor either small medium or large leaflets. For example, if small leaflets are desired, the upper left button 284 corresponding to row 286*a* (priority 1—high) and column 288*a* (large leaflets) is actuated. If there is a secondary preference for medium sized leaflets, then the button 284 corresponding to row 286*b* (priority 2—medium) and column 288*b* (medium leaflets) is actuated. By default, therefore, the large leaflets column 286*c* will be relegated to priority 3 (low), and the button corresponding to row 286*ac* and column 288*c* will be actuated.

The upper right portion of the parameter screen in FIG. 15 includes a leaflet size needed display and control box 290. As indicated above with respect to FIGS. 3 and 4 in the discussion of leaflet sizes relative to measured sheet thickness, there are different leaflet sizes associated with each thickness range. That is, differently sized leaflets can be formed from a particular portion of sheet having a measured thickness. Specifically, in the illustrated embodiment there are three leaflet sizes (19, 21, and 23 mm) for the small thickness range, two sizes (25 and 27 mm) for the medium thickness range, and three sizes (29, 31, and 33 mm) for the large thickness range. Without the display and control box 290, the system 100 might produce an excessive number of any one particular sized leaflet while neglecting another size.

The three columns 292*a*, 292*b*, and 292*c* each correspond to one of the thickness ranges, with the different sized leaflets separated within each column in the rows 294*a*, 294*b*, and 294*c*. At the intersection of each column 292 and row 294, a display indicating the number of leaflets needed for a particular size is provided. For example, the number of size 19 mm leaflets that are needed is indicated as 100. To alter the number needed for any of the sizes, the operator need only touch that particular button on the screen and a small keypad (not shown) will appear permitting modification thereof. In FIG. 15, therefore, the displays indicate that 100 leaflets are needed for each of the sizes in the small thickness range, 500 leaflets are needed for each of the sizes in the medium thickness range, and 300 leaflets are needed for each of the sizes in the large thickness range.

Display and control buttons 296 below each of the columns 292 indicate the percent yield adjust for each thickness range. When measuring and mapping biological tissue material, such as pericardial sac, the system 100 may not recognize visual defects. Therefore, an adjustment must be made to compensate for sheet material that is subsequently discarded based on visual inspection. For example, the large size range column indicates the percent yield adjust button 296 at 90%. That 90% corresponds to a discard level from subsequent visual inspection of 10%. Consequently, because 900 total zones within the large thickness range are required for leaflet cutting, the system will actually map and mark a total of about 1000 zones. In turn, the display of the number of zones actually marked will exceed the number needed as long as the percent yield adjust is less than 100%. Subsequently, 10% (i.e. 100) of the 1000 zones actually mapped and marked will be discarded, leaving 900 usable zones.

Just below the display and control box 290, a production values display 298 is provided which mirrors the production requirements display 264 of FIG. 14. Again, the production values display 298 helps the operator adjust the leaflet size needed display and control box 290 "on-the-fly." A vendor select button 300, and a vendor display 302 are seen on the left side of the system parameter screen. A reset counter 304 enables the operator to zero out the "marked" values in the production values display 298. The values in the column for leaflets "needed" default to those values entered in the leaflet size needed display and control box 290. When pressing the reset counter 304, a separate pop-up window (not shown) asks for confirmation that this action is desired.

Towards the bottom of the system parameter screen of FIG. 15, a display 306 of the number of leaflets found in the three size ranges in the last sac that was measured is provided. The navigational buttons 308 and the fault display 310 are essentially the same as those described for FIG. 15.

FIG. 16 illustrates a calibration screen, with the title of the screen displayed at 320. The mode buttons 322 are repeated here and have the same function as was described for the same buttons in FIG. 14. On both the left and right sides of the screen, a series of five buttons 324, 326, 328, 330, and 332 are provided to select the calibration operation. Again, two sets of buttons on the left and right are provided corresponding to the two workpiece carriages 132. The lineup button 324 performs set up for the marking head 114. The individual calibration button 326 performs an individual calibration on all the sensors 160. The values for each of the sensors are displayed along the display line 340 (exemplary values are omitted for clarity). The next three buttons, 328, 330, 332, perform calibrations on the sensors 160, with the corresponding values being displayed along the display lines 342, 344, and 346, respectively. Each of these calibration operations causes the array of sensors 160 to collectively contact a different elevational surface 190 on the calibration bar 188. Specifically, the button 328 causes the sensors 160 to contact the surface 190 corresponding to the high end of the high thickness range, the button 330 causes the sensors 160 to contact the surface 190 corresponding to the low end of the low thickness range, and the button 332 causes the sensors 160 to contact the surface 190 corresponding to the zero reference on the calibration bar 188 (typically performed first).

The calibrate button 334 performs all four calibration procedures in sequence automatically. The mode button 322 corresponding to CAL MODE must be actuated for this operation. Actuating the INK CONFIRM button 336 sequences the marking head 114 to insure dye is present for mapping. Again, the navigational buttons 348, and fault display 350 are as described above.

General Advantages

Certain advantages of the present invention are listed below:

improved process control—reduced operator judgment; consistent identification of bio-material sheet thickness from which to locate leaflet cut out sites;

systematic automated mapping/marking process: enables the inclusion of all possible leaflet cut out sections and reduces the number of intermediate steps required to produce a leaflet (i.e., subsectioning, tissue sorting);

inventory control—better control on selectivity of leaflet sizes required;

multiple points within a bio-material sheet can be measured for thickness by an array of programmable linear actuators and a three-axis computer-controlled positioning system;

sheet thickness is measured by an automatic "height" gauge using a linear actuator with programmable control of position, speed, acceleration and force;

after the thickness measurement, the bio-material sheet is marked by a high-performance dispenser with a biocompatible and toxicity-free reagent.

While the foregoing is a complete description of the preferred embodiments of the invention, various alternatives, modifications, and equivalents may be used. It will be obvious that certain other modifications may be practiced within the scope of the appended claims.

What is claimed is:

1. A method of inventory control of a bio-material for use in implants, comprising:

providing an inventory supply of a bio-material;

measuring the thickness of a plurality of points on a plurality of flattened elements of bio-material from the inventory supply;

inputting the measured thicknesses to a computer;

providing the computer with data regarding a preferred thickness of the flattened elements of bio-material for the implant; and cutting the flattened elements of bio-material into discrete zones based on the measured thickness and preferred thickness data so as to control the number of discrete zones of the preferred thickness that are cut from the inventory supply.

2. The method of claim 1, further including:

providing a human-machine interface enabling the computer to be manually supplied with a value of a preferred thickness of the flattened elements of bio-material for the implants; and providing software loaded on the computer to analyze the measured thickness information and identify discrete areas of similar thickness on the flattened elements of bio-material, the software being configured to maximize the number of discrete zones of preferred thickness identified.

3. The method of claim 1, wherein the flattened elements of bio-material are planar.

4. The method of claim 1, wherein the flattened elements of bio-material are non-planar.

5. The method of claim 4, wherein the flattened elements of bio-material are tubular.

6. The method of claim 1, wherein the step of measuring the thickness is automated using a system that measures a plurality of points on each flattened element of bio-material simultaneously.

7. The method of claim 6, further including:

creating a topographical map of each flattened element of bio-material using the computer.

8. The method of claim 1, further including:
marking the discrete zones on each flattened element of bio-material using the measured thicknesses.

9. The method of claim 8, wherein the step of measuring the thickness is automated using a system that measures a plurality of points on each flattened element of bio-material simultaneously, and wherein the step of marking the discrete zones is automated using a marking system that functions in conjunction with the system that measures the thickness.

10. The method of claim 1, wherein the implant is a prosthetic heart valve, the data pertains to a preferred thickness of heart valve leaflet, and the discrete zones are sized so as to cut heart valve leaflets therefrom.

11. The method of claim 10, wherein the flattened elements of bio-material are sheets of bovine pericardium.

12. The method of claim 2, wherein the human-machine interface includes input choices that permit the preferred thickness data to be varied.

13. The method of claim 2, wherein the human-machine interface comprises a touch-screen monitor.

14. A method of measuring a bio-material for use in an implant, comprising:
providing a bio-material;
flattening the biomaterial on a sanitary reference surface;
measuring the thickness of a plurality of points on the flattened bio-material;
inputting the measured thicknesses to a computer; and
running software on the computer that identifies preferred areas on the bio-material to use in the implant based on the measured thicknesses.

15. The method of claim 14, further including:
marking the preferred on the bio-material using the measured thicknesses.

16. The method of claim 14, further including:
providing a human-machine interface enabling the computer to be manually supplied with a value of a preferred thickness of the bio-material for the implant; and
wherein the preferred areas are of similar thickness, and the software is configured to control the number of preferred areas identified.

17. The method of claim 16, wherein the human-machine interface comprises a touch-screen monitor.

18. The method of claim 14, further including:
cutting the flattened bio-material into discrete zones based on the measured thickness and preferred areas so as to control the number of discrete zones.

19. The method of claim 14, wherein the step of measuring the thickness of a plurality of points is automated using a system that measures the plurality of points simultaneously.

20. The method of claim 19, further including:
creating a topographical map of the flattened bio-material using software running on the computer.

21. The method of claim 19, wherein the system that measures includes:
a measurement head adapted to simultaneously measure the thickness of a plurality of points on the bio-material relative to the reference surface; and
a marking head for marking the preferred areas directly on the bio-material sheet.

22. The method of claim 14, wherein the bio-material is bovine pericardium and wherein the preferred areas are zones of similar thickness that are large enough from which to cut a heart valve leaflet.

23. The method of claim 22, further including:
maximizing the number of zones of the preferred thickness.

* * * * *